(12) United States Patent
Svetlov et al.

(10) Patent No.: US 7,611,858 B1
(45) Date of Patent: Nov. 3, 2009

(54) DETECTION OF CANNABINOID RECEPTOR BIOMARKERS AND USES THEREOF

(75) Inventors: Stanislav Svetlov, Gainesville, FL (US); Ronald L. Hayes, Gainesville, FL (US); Ka-Wang (Kevin) Wang, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 11/738,159

(22) Filed: Apr. 20, 2007

Related U.S. Application Data

(63) Continuation-in-part of application No. PCT/US2005/038185, filed on Oct. 21, 2005.

(60) Provisional application No. 60/620,790, filed on Oct. 21, 2004.

(51) Int. Cl.
*G01N 33/00* (2006.01)
*C07K 14/00* (2006.01)
*C11D 15/00* (2006.01)

(52) U.S. Cl. .................. 435/7.95; 530/350; 530/324

(58) Field of Classification Search ............... None
See application file for complete search history.

(56) References Cited

U.S. PATENT DOCUMENTS

| | | | |
|---|---|---|---|
| 4,366,241 A | 12/1982 | Tom et al. | |
| 4,376,110 A | 3/1983 | David et al. | |
| 4,517,288 A | 5/1985 | Giegel et al. | |
| 4,816,567 A | 3/1989 | Cabilly et al. | |
| 4,837,168 A | 6/1989 | de Jaeger et al. | |
| 5,030,015 A | 7/1991 | Baker et al. | |
| 5,045,694 A | 9/1991 | Beavis et al. | |
| 5,118,937 A | 6/1992 | Hillenkamp et al. | |
| 5,223,409 A | 6/1993 | Ladner et al. | |
| 5,403,484 A | 4/1995 | Ladner et al. | |
| 5,427,908 A | 6/1995 | Dower et al. | |
| 5,516,637 A | 5/1996 | Huang et al. | |
| 5,571,698 A | 11/1996 | Ladner et al. | |
| 5,580,717 A | 12/1996 | Dower et al. | |
| 5,658,727 A | 8/1997 | Barbas et al. | |
| 5,698,426 A | 12/1997 | Huse | |
| 5,719,060 A | 2/1998 | Hutchens et al. | |
| 5,733,743 A | 3/1998 | Johnson et al. | |
| 5,750,753 A | 5/1998 | Kimae et al. | |
| 5,780,225 A | 7/1998 | Wigler et al. | |
| 5,792,664 A | 8/1998 | Chait et al. | |
| 5,821,047 A | 10/1998 | Garrard et al. | |
| 5,969,108 A | 10/1999 | McCafferty et al. | |
| 6,225,047 B1 | 5/2001 | Hutchens et al. | |

FOREIGN PATENT DOCUMENTS

| | | |
|---|---|---|
| WO | WO 90/02809 A1 | 3/1990 |
| WO | WO 91/10737 A1 | 7/1991 |
| WO | WO 92/01047 A1 | 1/1992 |
| WO | WO 92/18619 A1 | 10/1992 |
| WO | WO 93/11236 A1 | 6/1993 |
| WO | WO 93/24834 A1 | 12/1993 |
| WO | WO 95/15982 A2 | 6/1995 |
| WO | WO 95/20401 A1 | 8/1995 |
| WO | WO 99/51773 A1 | 10/1999 |
| WO | WO 00/04389 A2 | 1/2000 |
| WO | WO 00/56934 A1 | 9/2000 |

OTHER PUBLICATIONS

Hansen et al., Journal of Neurochemistry, 78(6):1415-1427, 2001.*
Sañudo-Peña et al., Acta Pharmacologica Sinica, 20(12):1115-1120, Dec. 20, 1999.*
Wager-Miller et al., Chemistry and Physics of Lipids, 121(1-2):83-89, Dec. 2002.*

* cited by examiner

*Primary Examiner*—John D Ulm
*Assistant Examiner*—Stacey MacFarlane
(74) *Attorney, Agent, or Firm*—Saliwanchik, Lloyd & Saliwanchik

(57) ABSTRACT

Traumatic insult to the brain leads to a degradation of low molecular weight of cannabinoid type 1 receptor (CB1) and generation of high molecular weight complexes in the cortex and hippocampus, as assessed by both N-terminal and C-terminal specific antibodies. The formation and release of CB1 oligomers was dramatically increased into CSF within 1 hour following traumatic brain insult. Novel CB1 receptor-based, prognostic markers of traumatic brain injury and other forms of brain injury are disclosed. A method of repopulating damaged neural cells by proliferation of a subgroup of neural progenitor cells is described. Targeting CB1 receptors for therapeutic neuroprotection in TBI is also disclosed.

11 Claims, 14 Drawing Sheets

DETECTION OF CANNABINOID RECEPTOR BIOMARKERS AND USES THEREOF

CROSS-REFERENCE TO RELATED APPLICATIONS

The present application is a continuation-in-part of International Application Serial No. PCT/US2005/038185, filed Oct. 21, 2005, which claims the benefit of U.S. Provisional Patent Application No. 60/620,790, filed Oct. 21, 2004, both of which are hereby incorporated by reference herein in their entirety, including any figures, tables, nucleic acid sequences, amino acid sequences, or drawings.

This invention was made with government support under National Institutes of Health, NIDDK grant number DK 061649 and U.S. Army Medical Research & Material Command/DoD, grant number DAMD17-03-1-0066. The government has certain rights in the invention.

FIELD OF THE INVENTION

The present invention concerns identification of cannabinoid receptor biomarkers for diagnosis and identification of brain injury candidate therapeutic pharmaceutical compounds and compositions.

BACKGROUND OF THE INVENTION

Permanent injury to the central nervous system (CNS) occurs in a variety of medical conditions, and has been the subject of intense scientific scrutiny in recent years. It is known that the brain has high metabolic requirements, and that it can suffer permanent neurologic damage if deprived of sufficient oxygen (hypoxia) for even a few minutes. In the absence of oxygen (anoxia), mitochondrial production of ATP cannot meet the metabolic requirements of the brain, and tissue damage occurs. This process is exacerbated by neuronal release of the neurotransmitter glutamate, which stimulates NMDA (N-methyl-D-aspartate), AMPA ($\alpha$-amino-3-hydroxy-5-methyl-4-isoxazole propionate) and kainate receptors. Activation of these receptors initiates calcium influx into the neurons, and production of reactive oxygen species, which are potent toxins that damage important cellular structures such as membranes, DNA and enzymes.

The brain has many redundant blood supplies, which means that its tissue is seldom completely deprived of oxygen, even during acute ischemic events caused by thromboembolic events or trauma. A combination of the injury of hypoxia with the added insult of glutamate toxicity is therefore believed to be ultimately responsible for cellular death. Hence if the additive insult of glutamate toxicity can be alleviated, neurological damage could also be lessened. Antioxidants and anti-inflammatory agents have been proposed to reduce damage, but they often have poor access to structures such as the brain (which are protected by the blood brain barrier).

Cannabinoid receptors are important in the regulation of $F_c\gamma$ receptor responses of monocytes and macrophages. Cannabinoid receptors are expressed on lung epithelial cells. These cells are responsible for the secretion of mucins and inflammatory cytokines/chemokines in the lung and are thus intricately involved in the generation and progression of respiratory diseases. Cannabinoid receptors may be expressed on gut epithelial cells and hence regulate cytokine and mucin production and may be of clinical use in treating inflammatory diseases related to the gut. Cannabinoid receptors are also expressed on lymphocytes, a subset of leukocytes.

Up to now, two subtypes of cannabinoid receptors and a splice variant have been identified. The CB1 receptor (Nature 1990, 346, 561) and a splice variant CB1a (J. Biol. Chem. 1995, 270, 3726) are mainly localized in the central nervous system. The CB2 receptor was mainly found in the peripheral tissue, in particular in leucocytes, spleen and macrophages (Eur. J. Biochem. 1995, 232, 54). CB1 and CB2 receptors have seven transmembrane regions and belong to the family of G protein receptors. Both receptors are negatively coupled via $G_i/G_o$ protein to adenylate cyclase and possibly negatively coupled to the presynaptic release of glutamate [cf. J. Neurosci. 1996, 16, 4322]. CB1 receptors are moreover positively coupled to potassium channels and negatively coupled to N- and O-type calcium channels.

Brain injury, such as, cerebral apoplexy is a result of a sudden circulatory disorder of a human brain area with subsequent functional losses, with corresponding neurological and/or psychological symptoms. The causes of cerebral apoplexy can lie in cerebral hemorrhages (e.g. after a vascular tear in hypertension, arteriosclerosis and apoplectic aneurysms) and ischemias (e.g. due to a blood pressure drop crisis or embolism). The functional losses in the brain lead to a degeneration or destruction of the brain cells. After a cerebral vascular occlusion, only a part of the tissue volume is destroyed as a direct result of the restricted circulation and the decreased oxygen supply associated therewith. This tissue area designated as the infarct core can only be kept from dying off by immediate recanalization of the vascular closure, e.g. by local thrombolysis, and is therefore only limitedly accessible to therapy. The outer peripheral zone, also designated as the penumbra, also discontinues its function immediately after onset of the vascular occlusion, but is initially still adequately supplied with oxygen by the collateral supply and irreversibly damaged only after a few hours or even only after days. Since the cell death in this area does not occur immediately, a therapeutic opportunity reveals itself to block the unfavorable development of the course of the disease both after stroke and after trauma. However, without early diagnosis, the prognosis of such patients is poor.

There is thus, a need in the art appropriate, specific, inexpensive and simple diagnostic clinical assessments of nervous system injury severity and therapeutic treatment efficacy. Thus identification of neurochemical markers that are specific to or predominantly found in the nervous system (CNS (brain and spinal cord) and PNS), would prove immensely beneficial for both prediction of outcome and for guidance of targeted therapeutic delivery.

SUMMARY

The present invention provides neuronal protein markers that are differentially present in the samples of patients suffering from neural injury and/or neuronal disorders as compared to samples of control subjects. The present invention also provides sensitive and quick methods and kits that can be used as an aid for diagnosis of neural injury and/or neuronal disorders by detecting these markers. The measurement of these markers, alone or in combination, in patient samples provides information that a diagnostician can correlate with a probable diagnosis of the extent of neural injury such as in traumatic brain injury (TBI), subarachnoid hemorrhage, epilepsy, stroke, and other forms of brain injury.

In particular, it was found that CB1 receptors occur in the form of multimeric complexes in normal rat hippocampus and cortex, and that traumatic insult results in a rapid perturbation of CB1 receptor assembly. The most prominent forms of CB1 receptor recognized by N-terminal-specific antibody in normal rat cortex and hippocampus localized to 62-64 kDa and 80-82 kDa protein bands, which correspond likely to glycosylated CB1 receptor. High molecular weight complexes at 120-130 kDa, ~260 kDa and higher could be also detected by N-terminal-specific antibody. In contrast, antibody against C-terminal-specific fragment labeled several different molecular entities of CB1 receptor—at 42-44 kDa, 120-130 kDa and >260 KDa proteins. Traumatic insult to the brain led to a degradation of low molecular weight of CB1 receptor and generation of high molecular weight complexes in cortex and hippocampus, as assessed by both N-terminal and C-terminal specific antibody. Moreover, the formation and release of CB1 oligomers, mostly C-terminal fragment-specific, was dramatically increased into CSF within 1 hour following traumatic brain insult.

In a preferred embodiment, the invention provides biomarkers that are indicative of traumatic brain injury, subarachnoid hemorrhage, epilepsy, stroke, and other forms of brain injury, neuronal damage, neural disorders, brain damage, neural damage due to drug or alcohol addiction, diseases associated with the brain or nervous system, such as the central nervous system. Preferably, the biomarkers are proteins, fragments or derivatives thereof, and are associated with neuronal cells, brain cells or any cell that is present in the brain and central nervous system.

In a preferred embodiment, molecular mediators for directed manipulation of stem/progenitor cells important for cell therapy and stimulation of endogenous neurogenesis are identified. For example, pro-survival lipid lysophosphatidic acid (LPA) instigated clonal generation of mouse neurospheres via LPA receptor-dependent proliferation of AC133 positive neural progenitors. Given a structural and receptor homology between LPA and endocannabinoids anandamide (AEA) and 2-arachidonoyl glycerol (2-AG), the endocannabinoid system may play a role in development of neural progenitors. A strong expression of cannabinoid receptors CB1 was found in mouse clonal neurospheres generated by EGF/FGF2 or LPA. CB1 receptor was expressed in the core of neurosphere and partially co-localized with LPA receptor and AC133. In neurospheres differentiated on an adherent matrix with EGF/FGF2, CB1 expression was restricted to cells of neuronal lineage. In contrast, neurospheres developed in the presence of LPA accumulated CB1 receptor in clusters of AC133 positive primitive progenitors.

In a preferred embodiment the biomarkers are preferably cannabinoid receptor proteins, complexes, peptides, fragments or variants thereof.

In another preferred embodiment, the invention provides variants of the polypeptide compositions described herein. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequence set forth herein.

In one preferred embodiment, the polypeptide fragments and variants provided by the present invention are immunologically reactive with an antibody and/or T-cell that reacts with a full-length polypeptide.

In another preferred embodiment, the polypeptide fragments and variants provided by the present invention exhibit a level of immunogenic activity of at least about 50%, preferably at least about 70%, and most preferably at least about 90% or more of that exhibited by a full-length polypeptide sequence specifically set forth herein.

In another preferred embodiment an expanded panel of biomarkers are used to provide highly enriched information of mechanism of injury, modes of cell death (necrosis versus apoptosis), sites of injury, sites and status of different cell types in the nervous system and enhanced diagnosis (better selectivity and specificity). This invention is an important and significant improvement over existing technologies focused on small panel (e.g. a four-marker panel:-MBP-Thrombomodulin-S100B-NSE from Syn X Pharma (Mississauga, Canada)- or single markers (e.g. S100B from DiaSorin (Sweden)).

The markers are characterized by molecular weight, enzyme digested fingerprints and by their known protein identities. The markers can be resolved from other proteins in a sample by using a variety of fractionation techniques, e.g., chromatographic separation coupled with mass spectrometry, or by traditional immunoassays. In preferred embodiments, the method of resolution involves Surface-Enhanced Laser Desorption/Ionization ("SELDI") mass spectrometry, in which the surface of the mass spectrometry probe comprises adsorbents that bind the markers.

In other preferred embodiments, a plurality of the biomarkers are detected, preferably at least two of the biomarkers are detected, more preferably at least three of the biomarkers are detected, most preferably at least four of the biomarkers are detected.

In one aspect, the amount of each biomarker is measured in the subject sample and the ratio of the amounts between the markers is determined. Preferably, the amount of each biomarker in the subject sample and the ratio of the amounts between the biomarkers and compared to normal healthy individuals. The increase in ratio of amounts of biomarkers between healthy individuals and individuals suffering from injury is indicative of the injury magnitude, disorder progression as compared to clinically relevant data.

Preferably, biomarkers that are detected at different stages of injury and clinical disease are correlated to assess anatomical injury, type of cellular injury, subcellular localization of injury. Monitoring of which biomarkers are detected at which stage, degree of injury in disease or physical injury will provide panels of biomarkers that provide specific information on mechanisms of injury, identify multiple subcellular sites of injury, identify multiple cell types involved in disease related injury and identify the anatomical location of injury.

In another aspect, preferably a single biomarker is used in combination with one or more biomarkers from normal, healthy individuals for diagnosing injury, location of injury and progression of disease and/or neural injury, more preferably a plurality of the markers are used in combination with one or more biomarkers from normal, healthy individuals for diagnosing injury, location of injury and progression of disease and/or neural injury. It is preferred that one or more protein biomarkers are used in comparing protein profiles from patients susceptible to, or suffering from disease and/or neural injury, with normal subjects.

Preferred detection methods include use of a biochip array. Biochip arrays useful in the invention include protein and nucleic acid arrays. One or more markers are immobilized on the biochip array and subjected to laser ionization to detect the molecular weight of the markers. Analysis of the markers is, for example, by molecular weight of the one or more markers against a threshold intensity that is normalized against total ion current. Preferably, logarithmic transformation is used for reducing peak intensity ranges to limit the number of markers detected.

In another preferred method, data is generated on immobilized subject samples on a biochip array, by subjecting said biochip array to laser ionization and detecting intensity of signal for mass/charge ratio; and, transforming the data into computer readable form; and executing an algorithm that classifies the data according to user input parameters, for detecting signals that represent markers present in injured and/or diseased patients and are lacking in non-injured and/or diseased subject controls.

Preferably the biochip surfaces are, for example, ionic, anionic, comprised of immobilized nickel ions, comprised of a mixture of positive and negative ions, comprises one or more antibodies, single or double stranded nucleic acids, comprises proteins, peptides or fragments thereof, amino acid probes, comprises phage display libraries.

In other preferred methods one or more of the markers are detected using laser desorption/ionization mass spectrometry, comprising, providing a probe adapted for use with a mass spectrometer comprising an adsorbent attached thereto, and; contacting the subject sample with the adsorbent, and; desorbing and ionizing the marker or markers from the probe and detecting the deionized/ionized markers with the mass spectrometer.

Preferably, the laser desorption/ionization mass spectrometry comprises, providing a substrate comprising an adsorbent attached thereto; contacting the subject sample with the adsorbent; placing the substrate on a probe adapted for use with a mass spectrometer comprising an adsorbent attached thereto; and, desorbing and ionizing the marker or markers from the probe and detecting the desorbed/ionized marker or markers with the mass spectrometer.

The adsorbent can for example be, hydrophobic, hydrophilic, ionic or metal chelate adsorbent, such as, nickel or an antibody, single- or double stranded oligonucleotide, amino acid, protein, peptide or fragments thereof.

In another embodiment, a process for purification of a biomarker, comprising fractioning a sample comprising one or more protein biomarkers by size-exclusion chromatography and collecting a fraction that includes the one or more biomarker; and/or fractionating a sample comprising the one or more biomarkers by anion exchange chromatography and collecting a fraction that includes the one or more biomarkers. Fractionation is monitored for purity on normal phase and immobilized nickel arrays. Generating data on immobilized marker fractions on an array, is accomplished by subjecting said array to laser ionization and detecting intensity of signal for mass/charge ratio; and, transforming the data into computer readable form; and executing an algorithm that classifies the data according to user input parameters, for detecting signals that represent markers present in injured and/or diseased patients and are lacking in non-injured and/or diseased subject controls. Preferably fractions are subjected to gel electrophoresis and correlated with data generated by mass spectrometry. In one aspect, gel bands representative of potential markers are excised and subjected to enzymatic treatment and are applied to biochip arrays for peptide mapping.

In another preferred embodiment, the presence of certain biomarkers is indicative of the extent of CNS and/or brain injury, subarachnoid hemorrhage, epilepsy, stroke, and other forms of brain injury. For example, detection of one or more cannabinoid receptor molecule, fragments, variants or derivatives thereof would be indicative of CNS injury and the presence of one or more would be indicative of the extent of nerve injury.

Preferred methods for detection and diagnosis of CNS/PNS and/or brain injury comprise detecting at least one or more protein biomarkers in a subject sample, and; correlating the detection of one or more protein biomarkers with a diagnosis of CNS and/or brain injury, wherein the correlation takes into account the detection of one or more biomarker in each diagnosis, as compared to normal subjects.

In another preferred embodiment, the invention provides a kit for analyzing cell damage in a subject. The kit, preferably includes: (a) a substrate for holding a biological sample isolated from a human subject suspected of having CNS and/or PNS damage, (b) an agent that specifically binds at least one or more of the neural cannabinoid receptor proteins; and (c) printed instructions for reacting the agent with the biological sample or a portion of the biological sample to detect the presence or amount of at least one marker in the biological sample.

Preferably, the biological sample is a fluid in communication with the nervous system of the subject prior to being isolated from the subject; for example, CSF or blood, and the agent can be an antibody, aptamer, or other molecule that specifically binds at least one or more of the neural proteins. The kit can also include a detectable label such as one conjugated to the agent, or one conjugated to a substance that specifically binds to the agent (e.g., a secondary antibody).

Other aspects of the invention are described infra.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

FIG. 5A shows a neurosphere grown in suspension for 3 weeks. FIG. 5B shows an adherent developing neurosphere for 1 week.

DETAILED DESCRIPTION

Figure 1:
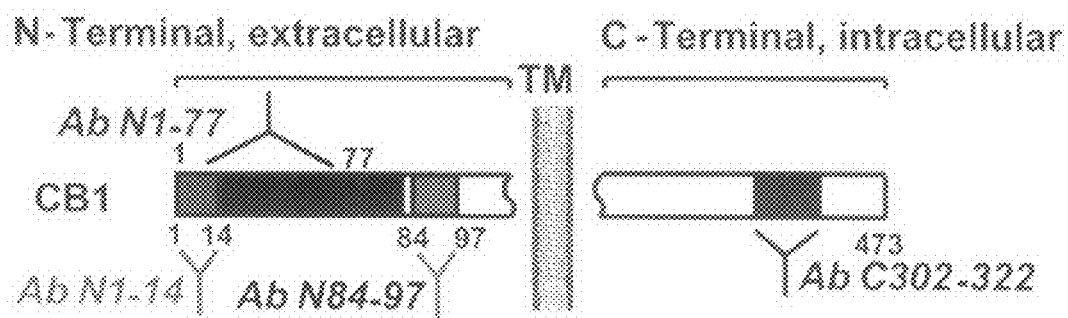
FIG. 1 is a schematic illustration showing the CB1 antibody recognition sites at different N- and C-terminal motifs of rat CB1 and CB1A receptor.
Figure 2A:
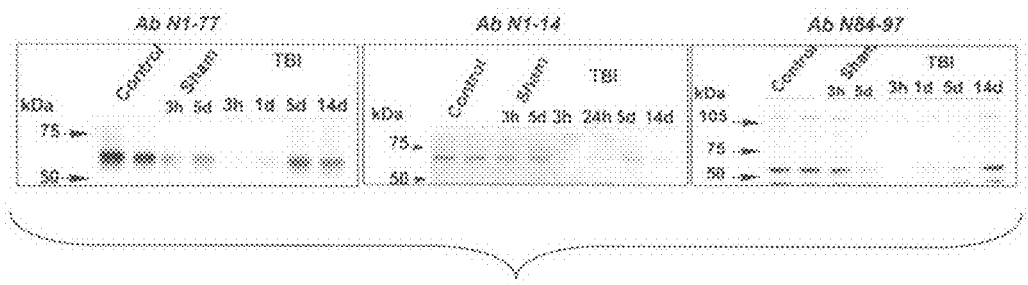
FIG. 2 is a graph showing the results obtained with CB1 Abs against N1-14 and N1-77 terminal motifs recognized mainly 62-64 kDa band in both cortex (FIG. 2A) and hippocampus (FIG. 2B). The N84-97 domain-specific CB1 Abs labeled also a 120-130 kDa protein in the cortex in addition to 62-64 kDa CB1 protein. These proteins degraded upon traumatic insult in a time-dependent fashion and accumulated in CSF as ~260 kDa and 120-130 kDa proteins (FIG. 2C) Quantitative analysis of CB1(N) in CSF with Av N1-77 is shown in FIG. 2D and with AvN84-97 in FIG. 2E.
Figure 2B:
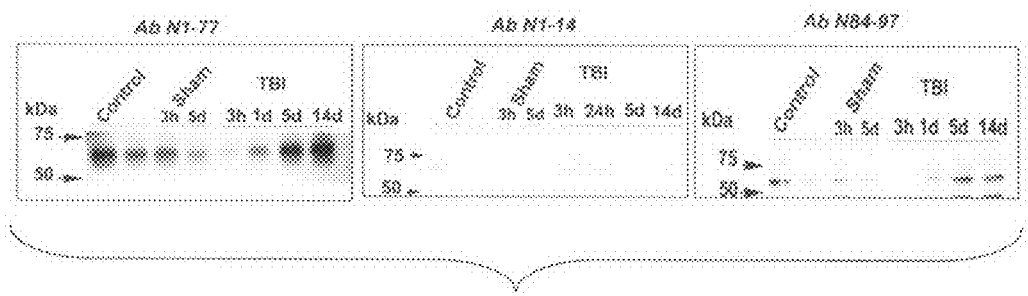
Figure 2C:
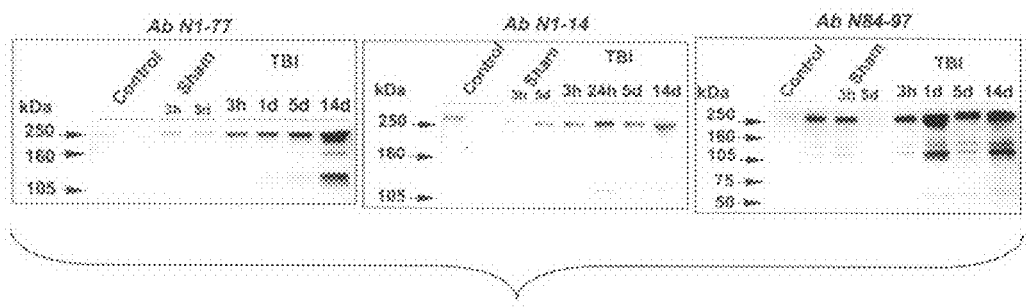
Figure 2D:
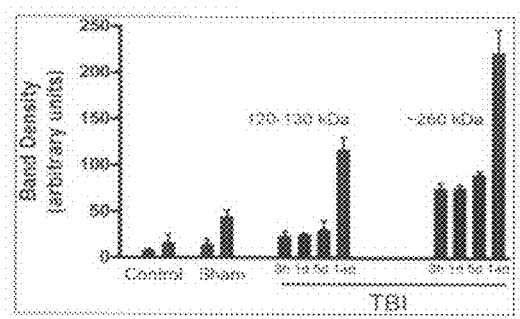
Figure 2E:
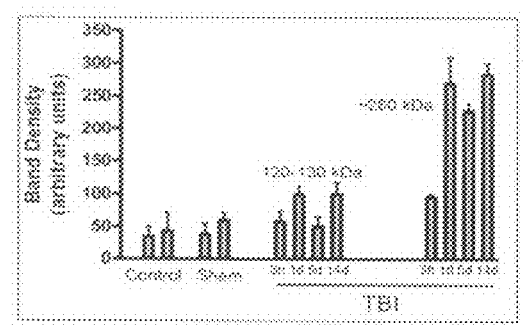
Figure 3A:
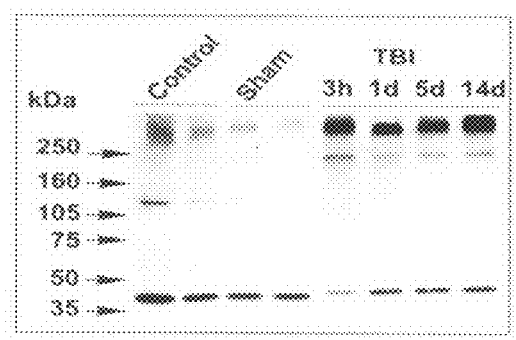
FIGS. 3A-3E are gels and graphs showing the results obtained with CB1 antibody against C-terminal domain recognized several molecular forms of CB1 immunoreactivity: ~42 kDa, 62-64 kDa, 120-130 kDa and >250 kDa cortex (FIG. 3A) hippocampus (FIG. 3B) and CSF (FIG. 3C). The 120-130 kDa protein decreased within 3 hours after TBI with concomitant accumulation of 260 kDa and >>260 kDa CB1 proteins (FIG. 3C). Intracellular C-domain-specific CB1 receptors accumulated in CSF as 120-130 kDa, ~260 kDa and >>260 kDa proteins (FIG. 3D).
Figure 3B:
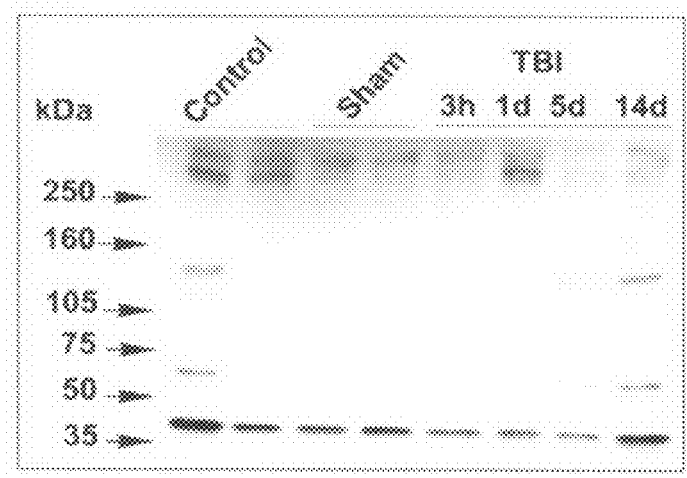
Figure 3C:
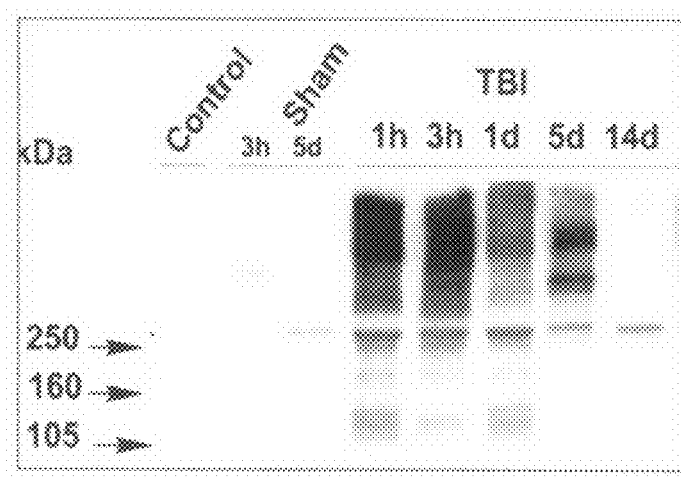
Figure 3D:
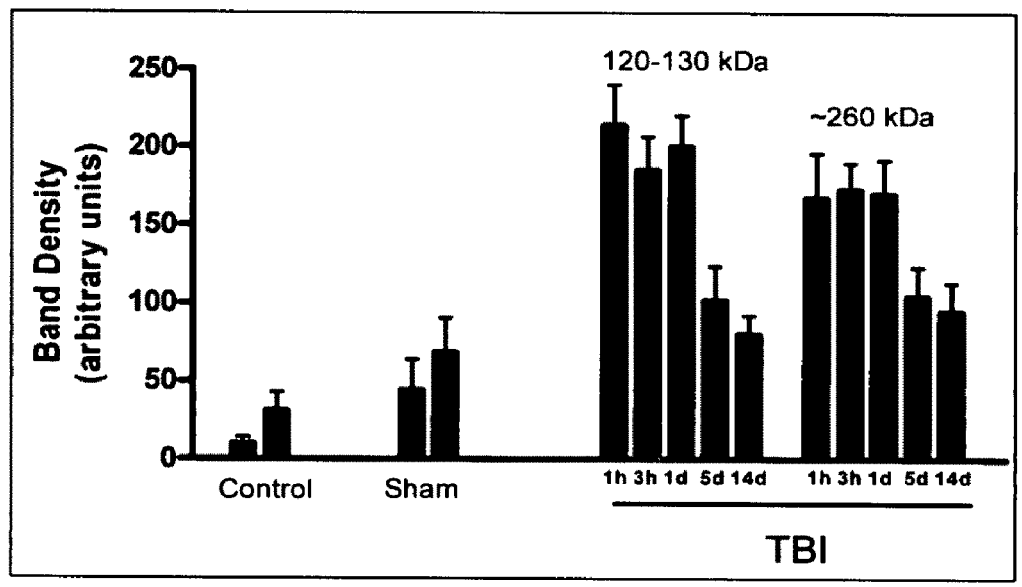
Figure 3E:
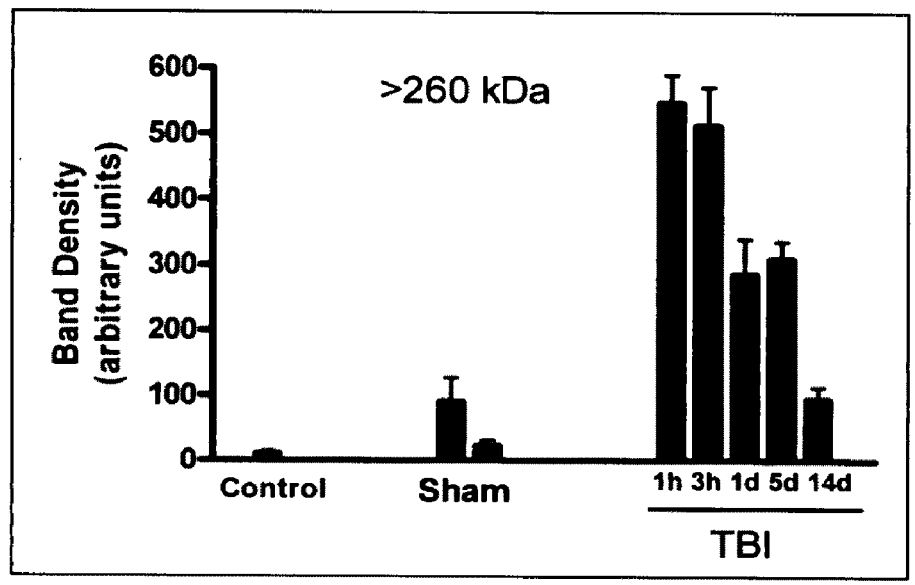
Figure 4A:
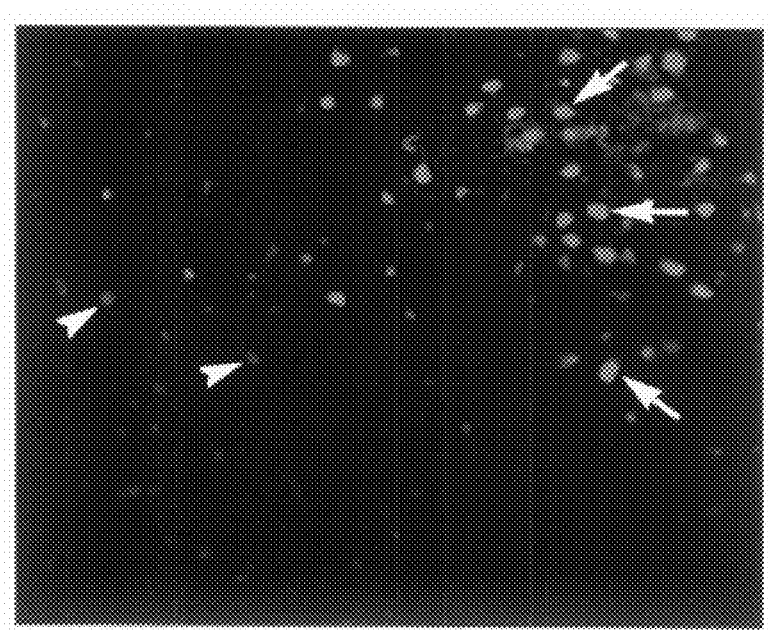
FIG. 4 shows quantitative analysis of CB1(C) accumulation in CSF and the results obtained using immunohistochemistry with N-terminal and C-terminal Abs which revealed a decrease in N-positive staining CB1 (N) NeuN (FIG. 4B) compared with control (FIG. 4A) and increase of C-terminal CB1 (C) NeuN (FIG. 4D) compared with control (FIG. 4C) accumulation in cortex and hippocampus after TBI. Shown: CB1 NeuN merged images Arrows: co-localization of CB1 and NeuN; arrowheads: lack of or partial co-localization.
Figure 4B:
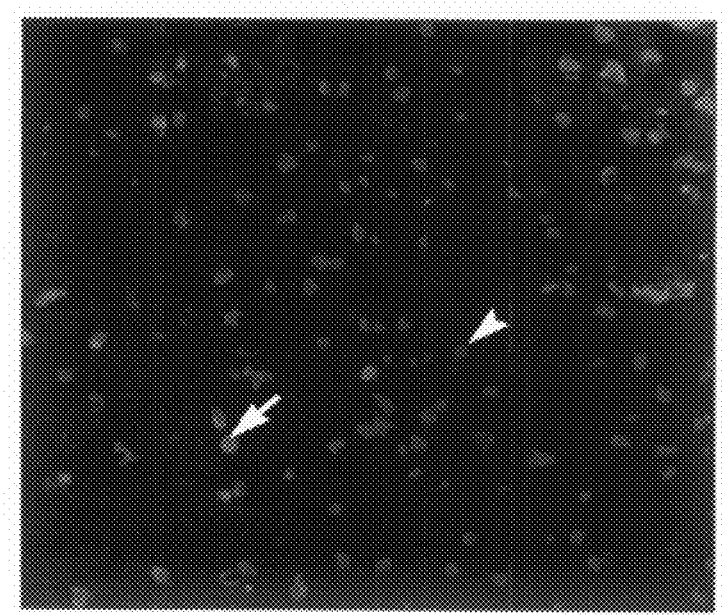
Figure 4C:
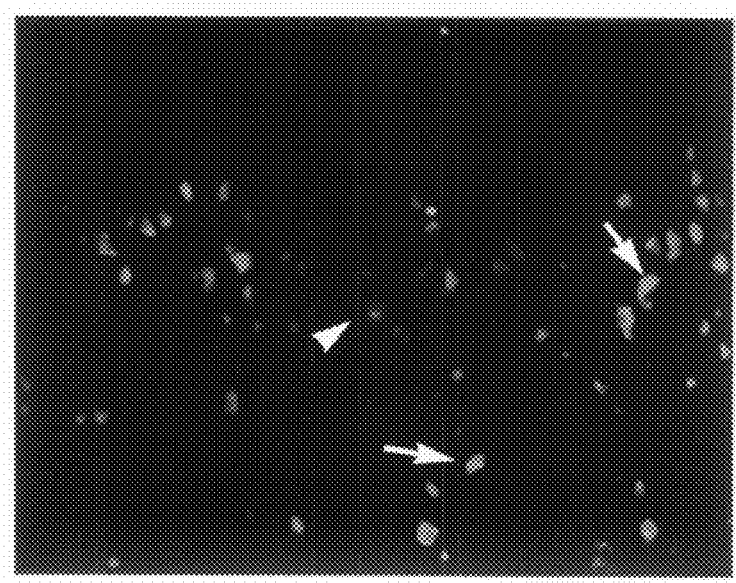
Figure 4D:
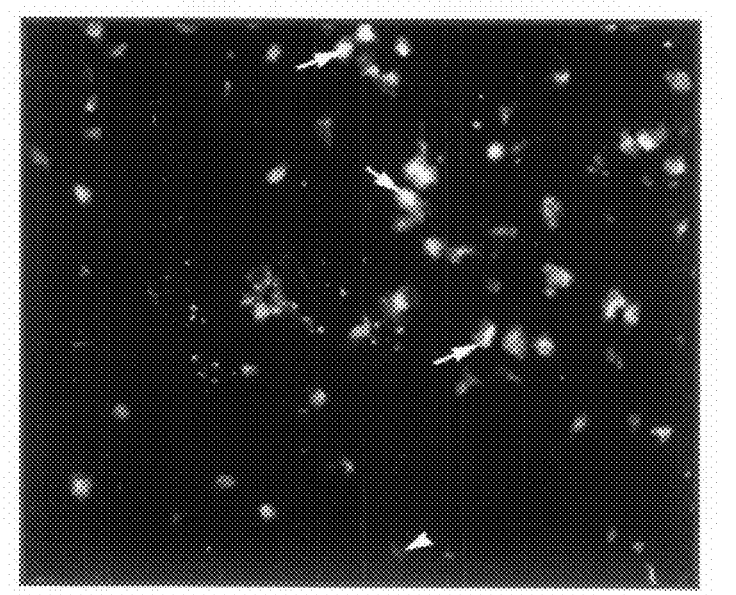

The present invention identifies biomarkers that are diagnostic of traumatic brain injury, central and peripheral nervous system injury. Detection of different cannabinoid receptor biomarkers of the invention are also diagnostic of the degree of severity of injury, the cell(s) involved in the injury, and the subcellular localization of the injury. In particular, the invention employs a step of correlating the presence or amount of one or more cannabinoid receptor protein(s) with the severity and/or type of brain cell injury. The amount of a cannabinoid receptor protein, fragment, variant, or derivative thereof directly relates to severity of brain tissue injury as more severe injury damages a greater number of brain cells which in turn causes a larger amount of cannabinoid receptor protein(s) to accumulate in the biological sample (e.g., CSF).

Prior to setting forth the invention, it may be helpful to an understanding thereof to set forth definitions of certain terms that will be used hereinafter.

"Marker" in the context of the present invention refers to a polypeptide (of a particular apparent molecular weight) which is differentially present in a sample taken from patients having brain, central and/or peripheral nervous system injury, and/or neural injury a as compared to a comparable sample taken from control subjects (e.g., a person with a negative diagnosis, normal or healthy subject).

"Complementary" in the context of the present invention refers to detection of at least two biomarkers, which when detected together provides increased sensitivity and specificity as compared to detection of one biomarker alone.

A "plurality" refers preferably to a group of at least about 5, more preferably, at least about 10, more preferably to a group of at least 100, more preferably to a group of at least 1,000 members. The maximum number of members is unlimited, but is at least 100,000 members.

The phrase "differentially present" refers to differences in the quantity and/or the frequency of a marker present in a sample taken from patients having for example, traumatic brain injury as compared to a control subject. For example, a marker can be a polypeptide which is present at an elevated level or at a decreased level in samples of patients with traumatic brain injury as compared to samples of control subjects. Alternatively, a marker can be a polypeptide which is detected at a higher frequency or at a lower frequency in samples of patients compared to samples of control subjects. A marker can be differentially present in terms of quantity, frequency or both.

A polypeptide is differentially present between the two samples if the amount of the polypeptide in one sample is statistically significantly different from the amount of the polypeptide in the other sample. For example, a polypeptide is differentially present between the two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively or additionally, a polypeptide is differentially present between the two sets of samples if the frequency of detecting the polypeptide in samples of patients' suffering from for example, traumatic brain injury, is statistically significantly higher or lower than in the control samples. For example, a polypeptide is differentially present between the two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

As used herein, nucleic acid "variants" refers to polynucleotide variants. Typically, polynucleotide variants will contain one or more substitutions, additions, deletions and/or insertions, preferably such that the immunogenicity of the polypeptide encoded by the variant polynucleotide is not substantially diminished relative to a polypeptide encoded by a polynucleotide sequence specifically set forth herein). The term "variants" should also be understood to encompasses homologous genes of xenogenic origin.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating their immunogenic activity as described herein using any of a number of techniques well known in the art.

As used herein, a "cannabinoid" is a chemical compound (such as cannabinol, THC or cannabidiol) that is found in the plant species *Cannabis saliva* (marijuana), and metabolites and synthetic analogues thereof that may or may not have psychoactive properties. Cannabinoids therefore include (without limitation) compounds (such as THC) that have high affinity for the cannabinoid receptor (for example $K_i$<250 nM), and compounds that do not have significant affinity for the cannabinoid receptor (such as cannabidiol, CBD). Cannabinoids also include compounds that have a characteristic dibenzopyran ring structure (of the type seen in THC) and cannabinoids which do not possess a pyran ring (such as cannabidiol). Hence a partial list of cannabinoids includes THC, CBD, dimethyl heptylpentyl cannabidiol (DMHP-CBD), 6,12-dihydro-6-hydroxy-cannabidiol; (3S, 4R)-7-hydroxy-$\delta^6$-tetrahydrocannabinol homologs and derivatives; (+)-4-[4-DMH-2,6-diacetoxy-phenyl]-2-carboxy-6,6-dimethylbicyclo[3.1.1]hept-2-en, and other 4-phenylpinene derivatives; and cannabidiol (−)(CBD) analogs such as (−)CBD-monomethylether, (−)CBD dimethyl ether; (−)CBD diacetate; (−)3'-acetyl-CBD monoacetate; and AF11.

"Diagnostic" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

An advantage of assays of the invention is that they may, if desired, be performed in "real time". As used herein in reference to monitoring, measurements or observations in assays of the invention, the term "real time" refers to that which is performed contemporaneously with the monitored, measured or observed events and which yields a result of the monitoring, measurement or observation to one who performs it simultaneously, or effectively so, with the occurrence of a monitored, measured or observed event. Thus, a "real time" assay or measurement contains not only the measured and quantitated result, such as fluorescence, but expresses this in real time, that is, in hours, minutes, seconds, milliseconds, nanoseconds, picoseconds, etc.

A "test amount" of a marker refers to an amount of a marker present in a sample being tested. A test amount can be either in absolute amount (e.g., µg/ml) or a relative amount (e.g., relative intensity of signals).

A "diagnostic amount" of a marker refers to an amount of a marker in a subject's sample that is consistent with a diagnosis of brain injury, neural injury, CNS/PNS injury. A diagnostic amount can be either in absolute amount (e.g., µg/ml) or a relative amount (e.g., relative intensity of signals).

A "control amount" of a marker can be any amount or a range of amount which is to be compared against a test amount of a marker. For example, a control amount of a marker can be the amount of a marker in a person without brain injury and/or neural injury. A control amount can be either in absolute amount (e.g., µg/ml) or a relative amount (e.g., relative intensity of signals).

"Probe" refers to a device that is removably insertable into a gas phase ion spectrometer and comprises a substrate having a surface for presenting a marker for detection. A probe can comprise a single substrate or a plurality of substrates.

"Substrate" or "probe substrate" refers to a solid phase onto which an adsorbent can be provided (e.g., by attachment, deposition, etc.).

"Adsorbent" refers to any material capable of adsorbing a marker. The term "adsorbent" is used herein to refer both to a single material ("monoplex adsorbent") (e.g., a compound or functional group) to which the marker is exposed, and to a plurality of different materials ("multiplex adsorbent") to which the marker is exposed. The adsorbent materials in a multiplex adsorbent are referred to as "adsorbent species." For example, an addressable location on a probe substrate can comprise a multiplex adsorbent characterized by many different adsorbent species (e.g., anion exchange materials, metal chelators, or antibodies), having different binding characteristics. Substrate material itself can also contribute to adsorbing a marker and may be considered part of an "adsorbent."

"Adsorption" or "retention" refers to the detectable binding between an absorbent and a marker either before or after washing with an eluant (selectivity threshold modifier) or a washing solution.

"Eluant" or "washing solution" refers to an agent that can be used to mediate adsorption of a marker to an adsorbent. Eluants and washing solutions are also referred to as "selectivity threshold modifiers." Eluants and washing solutions can be used to wash and remove unbound materials from the probe substrate surface.

"Resolve," "resolution," or "resolution of marker" refers to the detection of at least one marker in a sample. Resolution includes the detection of a plurality of markers in a sample by separation and subsequent differential detection. Resolution does not require the complete separation of one or more markers from all other biomolecules in a mixture. Rather, any separation that allows the distinction between at least one marker and other biomolecules suffices.

"Gas phase ion spectrometer" refers to an apparatus that measures a parameter which can be translated into mass-to-charge ratios of ions formed when a sample is volatilized and ionized. Generally ions of interest bear a single charge, and mass-to-charge ratios are often simply referred to as mass. Gas phase ion spectrometers include, for example, mass spectrometers, ion mobility spectrometers, and total ion current measuring devices.

"Mass spectrometer" refers to a gas phase ion spectrometer that includes an inlet system, an ionization source, an ion optic assembly, a mass analyzer, and a detector.

"Laser desorption mass spectrometer" refers to a mass spectrometer which uses laser as means to desorb, volatilize, and ionize an analyte.

"Detect" refers to identifying the presence, absence or amount of the object to be detected.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

"Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavidin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantify the amount of bound detectable moiety in a sample. Quantitation of the signal is achieved by, e.g., scintillation counting, densitometry, or flow cytometry.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'$_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "$F_c$" of an antibody refers to that portion of an immunoglobulin heavy chain that comprises one or more heavy chain constant region domains, $CH_1$, $CH_2$ and $C_3$, but does not include the heavy chain variable region.

"Immunoassay" is an assay that uses an antibody to specifically bind an antigen (e.g., a marker). The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to marker CB1 from specific species such as rat, mouse, or human can be selected to obtain only those polyclonal antibodies that are specifically immunoreactive with marker CB1 and not with other proteins, except for polymorphic variants and alleles of marker CB1. This selection may be achieved by subtracting out antibodies that cross-react with marker CB1 molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

"Energy absorbing molecule" or "EAM" refers to a molecule that absorbs energy from an ionization source in a mass spectrometer thereby aiding desorption of analyte, such as a marker, from a probe surface. Depending on the size and nature of the analyte, the energy absorbing molecule can be optionally used. Energy absorbing molecules used in MALDI are frequently referred to as "matrix." Cinnamic acid derivatives, sinapinic acid ("SPA"), cyano hydroxy cinnamic acid ("CHCA") and dihydroxybenzoic acid are frequently used as energy absorbing molecules in laser desorption of bioorganic molecules.

"Sample" is used herein in its broadest sense. A sample comprising polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

"Substantially purified" refers to nucleic acid molecules or proteins that are removed from their natural environment and are isolated or separated, and are at least about 60% free, preferably about 75% free, and most preferably about 90% free, from other components with which they are naturally associated.

"Substrate" refers to any rigid or semi-rigid support to which nucleic acid molecules or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

As used herein, the term "injury" or "neural injury" is intended to include a damage which directly or indirectly affects the normal functioning of the CNS. For example, the injury can be damage or retinal ganglion cells; a traumatic brain injury; a stroke related injury; a cerebral aneurism related injury; a spinal cord injury, including monoplegia, diplegia, paraplegia, hemiplegia and quadriplegia; a neuroproliferative disorder, neuropathic pain syndrome, subarachnoid hemorrhage, epilepsy, stroke, and other forms of brain injury. Examples of CNS injuries or disease include TBI, stroke, concussion (including post-concussion syndrome), cerebral ischemia, neurodegenerative diseases of the brain such as Parkinson's disease, Dementia Pugilistica, Huntington's disease and Alzheimer's disease, Creutzfeldt-Jakob disease, brain injuries secondary to seizures which are induced by radiation, exposure to ionizing or iron plasma, nerve agents, cyanide, toxic concentrations of oxygen, neurotoxicity due to CNS malaria or treatment with anti-malaria agents, and other CNS traumas.

As used herein, the term "Traumatic Brain Injury" is art recognized and is intended to include the condition in which, a traumatic blow to the head causes damage to the brain, often without penetrating the skull. Usually, the initial trauma can result in expanding hematoma, subarachnoid hemorrhage, cerebral edema, raised intracranial pressure (ICP), and cerebral hypoxia, which can, in turn, lead to severe secondary events due to low cerebral blood flow (CBF).

"Neural cells" as defined herein, are cells that reside in the brain, central and peripheral nerve systems, including, but not limited to, nerve cells, glial cell, oligodendrocyte, microglia cells or neural stem cells.

"Neural (neuronal) defects, disorders or diseases" as used herein refers to any neurological disorder, including but not limited to neurodegenerative disorders (Parkinson's; Alzheimer's) or autoimmune disorders (multiple sclerosis) of the central nervous system; memory loss; long term and short term memory disorders; learning disorders; autism, depression, benign forgetfulness, childhood learning disorders, close head injury, and attention deficit disorder; autoimmune disorders of the brain, neuronal reaction to viral infection; brain damage; depression; psychiatric disorders such as bipolarism, schizophrenia and the like; narcolepsy/sleep disorders (including circadian rhythm disorders, insomnia and narcolepsy); severance of nerves or nerve damage; severance of the cerebrospinal nerve cord (CNS) and any damage to brain or nerve cells; neurological deficits associated with AIDS; tics (e.g. Giles de la Tourette's syndrome); Huntington's chorea, schizophrenia, traumatic brain injury, tinnitus, neuralgia, especially trigeminal neuralgia, neuropathic pain, inappropriate neuronal activity resulting in neurodysthesias in diseases such as diabetes, MS and motor neuron disease, ataxias, muscular rigidity (spasticity) and temporomandibular joint dysfunction; Reward Deficiency Syndrome (RDS) behaviors in a subject.

As used herein, a "pharmaceutically acceptable" component is one that is suitable for use with humans and/or animals without undue adverse side effects (such as toxicity, irritation, and allergic response) commensurate with a reasonable benefit/risk ratio.

The terms "patient" or "individual" are used interchangeably herein, and is meant a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

As used herein, "ameliorated" or "treatment" refers to a symptom which is approaches a normalized value, e.g., is less than 50% different from a normalized value, preferably is less than about 25% different from a normalized value, more preferably, is less than 10% different from a normalized value, and still more preferably, is not significantly different from a normalized value as determined using routine statistical tests.

Cannabinoid Receptor Biomarkers

Endocannabinoids anandamide and 2-arachidonylglycerol (2-AG) act in CNS via G protein coupled CB1 receptors. CB1 receptors may exist in the rat brain as dimeric or oligomeric form. In this study, brain cortex and hippocampus of rats subjected to controlled cortical impact using antibody generated against N-terminal and C-terminal fragments of CB1 receptors, was analyzed. By using western blot, immunoprecipitation and immunohistochemistry, it is shown that CB1 receptors occur mostly in the form of multimeric complexes in normal rat hippocampus and cortex, and that traumatic insult results in a rapid perturbation of CB1 receptor assembly. The most prominent forms of CB1 receptor recognized by N-terminal-specific antibody in normal rat cortex and hippocampus localized to 62-64 kDa and 80-82 kDa protein bands, which correspond likely to glycosylated CB1 receptor. High molecular weight complexes at 120-130 kDa, ~260 kDa and higher could be also detected by N-terminal-specific antibody. In contrast, antibody against C-terminal-specific fragment labeled several different molecular entities of CB1 receptor—at 42-44 kDa, 120-130 kDa and >260 KDa proteins. Traumatic insult to the brain led to a degradation of low molecular weight of CB1 receptor and generation of high molecular weight complexes in cortex and hippocampus, as assessed by both N-terminal and C-terminal specific antibody. Moreover, the formation and release of CB1 oligomers, mostly C-terminal fragment-specific, was dramatically increased into CSF within 1 hour following traumatic brain insult. The data suggest that oligomerization of CB1 receptor, which involves primarily intracellular, C-terminal motif-dependent mechanism(s) of the molecule plays a role in both normal brain physiology and in pathogenesis of TBI. Collectively, these results provide rationale for development of CB1 receptor-based, prognostic markers of traumatic brain injury in addition to targeting CB1 receptor for possible therapeutic neuroprotection in TBI.

In a preferred embodiment, detection of one or more brain injury biomarkers is diagnostic of neural damage and/or neuronal disease. Examples of brain injury biomarkers, include but are not limited to: cannabinoid receptors, fragments and variants thereof, such as CB1 and C-terminal complexes of CB1. Without wishing to be bound by theory, upon injury, structural and functional integrity of the cell membrane and blood brain barrier are compromised. Brain-specific and brain-enriched proteins are released into the extracellular space and subsequently into the CSF and blood and detected by the methods and compositions disclosed herein.

In a preferred embodiment, detection of at least one C-terminal CB1 complex biomarker in CSF, blood, or other biological fluids, is diagnostic of the severity of brain injury, subarachnoid hemorrhage, epilepsy, stroke, and other forms of brain injury and/or the monitoring of the progression of therapy. Preferably, the cannabinoid receptor C-terminal complexes are detected during the early stages of injury. An increase in the amount of such complexes, fragments or variants thereof, in a patient suffering from a neural injury, neuronal disorder as compared to a normal healthy individual, will be diagnostic of a neural injury and/or neuronal disorder.

In another preferred embodiment, detection of at least two C-terminal CB1 receptor biomarker in CSF, blood, or other biological fluids, is diagnostic of the severity of injury following a variety of CNS insults, such as for example, stroke, spinal cord injury, subarachnoid hemorrhage, epilepsy, stroke, and other forms of brain injury or neurotoxicity caused by alcohol or substance abuse (e.g. ecstasy, methamphetamine, etc.)

In another preferred embodiment, the detection of at least one C-terminal cannabinoid receptor biomarker, fragments or variants thereof are correlated with a known protein such as cannabinoid receptor 1.

In another preferred embodiment, the invention provides for the quantitative detection of damage to the CNS, PNS and/or brain injury at a subcellular level. Depending on the type and/or amount of C-terminal complex cannabinoid receptor biomarker detected, is indicative of the severity of injury. Located primarily in the brain, CB1 receptors are associated with behavioral, psychological, cognitive, and physiological effects. The human brain contains a larger number of CB1 receptors than is typically found with other G-protein-coupled receptor types. For example, there are 10 times more CB1 receptors than mu opioid receptors, the receptor for morphine.

In another preferred embodiment, cell-type specific cannabinoid receptor biomarkers are identified by cannabinoids. Cannabinoids are believed to have an overall inhibitory effect on neurotransmission, although this effect is variable. In some circumstances neurotransmission can be inhibited by cannabinoids, yet in other circumstances it can be stimulated. For example, cannabinoid receptors on presynaptic neurons, inhibit the release of gamma-aminobutyric acid (GABA) and stimulate neurotransmission. When they are located on postsynaptic neurons, they mimic the effects of GABA and inhibit neurotransmission. Thus, the effects of cannabinoids vary by location.

In preferred embodiments, identification of specific cannabinoid receptors, C-terminal complexes, fragments and variants thereof are isolated and mapped in the human brain, thereby providing specific biomarkers determinative of cell injury. For example, by the methods disclosed herein, cell specific cannabinoid receptor biomarkers are identified in the amygdala, basal ganglia, brain stem, central gray, cerebellum, cerebral cortex (especially cingulate), hippocampus, hypothalamus, nucleus accumbens, nucleus of solitary tract, and spinal cord.

The ability to detect and monitor levels of these proteins after CNS injury provides enhanced diagnostic capability by allowing clinicians (1) to determine the level of injury severity in patients with various CNS injuries, (2) to monitor patients to signs of secondary CNS injuries that may elicit these cellular changes and (3) to monitor the effects of therapy by examination of these proteins in CSF or blood. Unlike other organ-based diseases where rapid diagnostics for surrogate biomarkers prove invaluable to the course of action taken to treat the disease, no such rapid, definitive diagnostic tests exist for traumatic or ischemic brain injury that might provide physicians with quantifiable neurochemical markers to help determine the seriousness of the injury, the anatomical and cellular pathology of the injury, and the implementation of appropriate medical management and treatment.

In comparison to currently existing products, the invention provides several superior advantages and benefits. First, the identification of cannabinoid receptor biomarkers provide more rapid and less expensive diagnosis of injury severity than existing diagnostic devices such as computed tomography (CT) and magnetic resonance imaging (MRI). The invention also allows quantitative detection and high content assessment of damage to the brain and/or CNS/PNS.

In another preferred embodiment, nerve cell damage in a subject is analyzed by (a) providing a biological sample isolated from a subject suspected of having, for example, traumatic brain injury; (b) detecting in the sample the presence or amount of at least one marker selected from one or more cannabinoid receptor biomarkers, fragments or variants thereof; C-terminal cannabinoid receptor complexes, fragments and variants thereof; and (c) correlating the presence or amount of the marker with the presence or type of nerve cell damage in the subject. Preferably, neural cells, such as those cells that reside in the central and peripheral nerve systems, including nerve cells, glial cell, oligodendrocyte, microglia cells or neural stem cells) in in vitro culture or in situ in an animal subjects express higher levels of cannabinoid receptor biomarkers as compared to non-neuronal cells, such as cardiomyocytes, myocytes in skeletal muscles, hepatocytes, kidney cells and cells in testis. Preferably, the samples comprise neural cells, for example, a biopsy of a central nervous system or peripheral nervous system tissue are suitable biological samples for use in the invention. In addition, after injury to the nervous system (such as brain injury), the neural cell membrane is compromised, leading to the efflux of these cannabinoid receptor biomarker proteins first into the extracellular fluid or space and to the cerebrospinal fluid and eventually in the circulating blood (as assisted by the compromised blood brain barrier) and other biofluids (e.g. urine, sweat, saliva, etc.). Thus, other suitable biological samples include, but not limited to such cells or fluid secreted from these cells. Obtaining biological fluids such as cerebrospinal fluid, blood, plasma, serum, saliva and urine, from a subject is typically much less invasive and traumatizing than obtaining a solid tissue biopsy sample. Thus, samples, which are biological fluids, are preferred for use in the invention. CSF, in particular, is preferred for detecting brain damage in a subject as it is in immediate contact with the nervous system and is readily obtainable.

A biological sample can be obtained from a subject by conventional techniques. For example, CSF can be obtained by lumbar puncture. Blood can be obtained by venipuncture, while plasma and serum can be obtained by fractionating whole blood according to known methods. Surgical techniques for obtaining solid tissue samples are well known in the art. For example, methods for obtaining a nervous system tissue sample are described in standard neuro-surgery texts such as Atlas of Neurosurgery: Basic Approaches to Cranial and Vascular Procedures, by F. Meyer, Churchill Livingstone, 1999; Stereotactic and Image Directed Surgery of Brain Tumors, 1st ed., by David G. T. Thomas, WB Saunders Co., 1993; and Cranial Microsurgery: Approaches and Techniques, by L. N. Sekhar and E. De Oliveira, 1st ed., Thieme Medical Publishing, 1999. Methods for obtaining and analyzing brain tissue are also described in Belay et al., *Arch. Neurol.* 58: 1673-1678 (2001); and Seijo et al., *J. Clin. Microbiol.* 38: 3892-3895 (2000).

Any animal can be used as a subject from which a biological sample is obtained. Preferably, the subject is a mammal, such as for example, a human, dog, cat, horse, cow, pig, sheep, goat, chicken, primate, rat, or mouse. More preferably, the subject is a human. Particularly preferred are subjects suspected of having or at risk for developing traumatic or non-traumatic nervous system injuries, such as victims of brain injury caused by traumatic insults (e.g. gunshots wounds, automobile accidents, sports accidents, shaken baby syndrome), ischemic events (e.g. stroke, cerebral hemorrhage, cardiac arrest), spinal cord injury, neurodegenerative disorders (such as Alzheimer's, Huntington's, and Parkinson's diseases; epilepsy, substance abuse (e.g., from amphetamines, methamphetamine/Speed, Ecstasy/MDMA, or ethanol and cocaine), and peripheral nervous system pathologies such as diabetic neuropathy, chemotherapy-induced neuropathy and neuropathic pain, peripheral nerve damage or atrophy (ALS), multiple sclerosis (MS, subarachnoid hemorrhage, epilepsy, stroke, and other forms of brain injury.

The invention is based upon the discovery that a natural binding domain, sequence or polypeptide, as defined above, associates with a binding partner to form a complex or dissociates from a binding partner, in a manner that is dependent upon the presence or absence of a phosphate moiety, and that is detectable and measurable in a highly sensitive manner that may be observed in real time.

The invention provides receptor molecules and assays for measuring the activity of protein kinases and phosphatases. These reporter molecules are naturally-occurring polypeptides which include natural binding domains, natural binding sequences and natural binding polypeptides, each as defined above, which are used in assays of the invention in combination with polypeptide binding partners, also as defined above.

Minimally, such a reporter molecule comprises or consists of a natural binding domain. The amino acids of a natural binding domain are those which are necessary for phosphorylation-dependent binding of the molecule comprising or consisting of the natural binding domain with a binding partner, whether such a partner is present on the same or a different polypeptide chain as the natural binding domain. Such amino acids may include points of direct contact between the domain and the binding partner, those which are recognized and/or modified (i.e., phosphorylated or dephosphorylated) by a kinase or phosphatase and those which maintain the three-dimensional structure or charge of the binding domain in a manner which permits phosphorylation and/or dephosphorylation and the consequent phosphorylation—and/or dephosphorylation-dependent binding of the domain to the binding partner. The amino acids of a natural binding domain may be contiguous or may be separated by non-domain amino acids; such non-domain residues may be either those which are naturally present between the amino acids of the natural binding domain or which are non-natural. In cases in which non-natural amino acids are found interspersed with those of a natural binding domain, such non-natural residues will be residues which do not substantially (that is, measurably) alter the natural phosphorylation-dependent binding of the natural binding domain to its binding partner.

A second reporter molecule of use in the invention is that which comprises a naturally-occurring stretch of contiguous amino acids sufficient for phosphorylation-dependent binding to a binding partner, as defined above, i.e., at least the minimum number of contiguous amino acids required to encompass a natural binding domain. The phosphorylationdependence of such a molecule, referred to herein as a "natural binding sequence", is, itself natural. A reporter molecule of the invention can comprise a natural binding sequence. Amino acids outside of the natural binding sequence do not substantially influence phosphorylation-dependent binding of the natural binding domain to the binding partner.

Lastly, a reporter molecule of use in the invention may be a "natural binding polypeptide", as defined above. Such a polypeptide molecule comprises multiple natural binding domains, which domains are, either individually or in concert with one another, sufficient to permit natural, phosphorylation-dependent binding of the natural binding polypeptide to a binding partner.

By monitoring the association or dissociation of a natural binding domain, sequence or polypeptide and its binding partner in the presence of a known or candidate protein kinase or phosphatase, the activity of such an enzyme can be measured. In such assays, one or both of the natural binding domain, sequence or polypeptide and its binding partner comprises a detectable label including, but not exclusively, a fluorescent or other light-emitting label, which may be either chemical or proteinaceous. By measuring changes in signal emission or absorption before and after addition to the mixture comprising the natural binding domain, sequence or polypeptide and its binding partner of the enzyme to be assayed, the extent of phosphorylation can be calculated. An important feature of the invention is that such measurements (e.g., of a shift in FRET) can be performed in real-time. This allows for sensitive assessment of enzyme reaction kinetics based upon the rate of change of the protein-binding-dependent signal emission or absorption by the label(s).

Assays in which the above reporter molecules are used according to the invention may be performed either in double- or single-chain format. In double-chain format, natural binding domain, sequence or polypeptide is comprised by a different polypeptide chain from that comprising the binding partner and is not otherwise covalently linked to it. In single-chain format, the natural binding domain, sequence or polypeptide is covalently linked to its binding partner, either through an intervening amino acid sequence or a chemical linker.

The binding partner of a natural binding domain, sequence or polypeptide may, itself, be a natural binding domain, sequence or polypeptide as defined herein. If so, binding of the two molecules may depend upon the phosphorylation state of one or both in a manner that is comparable to that found in nature.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y., which is incorporated herein by reference), chemical methods, pharmaceutical formulation and delivery and treatment of patients.

Methods to Detect Protein: Protein Binding in Assays of the Invention

Methods of detecting the phosphorylation-dependent binding of a natural binding domain, sequence or polypeptide and a binding partner in an assay of the invention most usefully, although not exclusively, are those which employ light-emitting labels. Several such techniques are described below.

Fluorescence Energy Resonance Transfer (FRET): A tool with which to assess the distance between one molecule and another (whether protein or nucleic acid) or between two positions on the same molecule is provided by the technique of fluorescence resonance energy transfer (FRET), which is now widely known in the art (for a review, see Matyus, 1992, *J. Photochem. Photobiol. B: Biol.,* 12: 323-337, which is herein incorporated by reference). FRET is a radiationless process in which energy is transferred from an excited donor molecule to an acceptor molecule; the efficiency of this transfer is dependent upon the distance between the donor an acceptor molecules. Since the rate of energy transfer is inversely proportional to the sixth power of the distance between the donor and acceptor, the energy transfer efficiency is extremely sensitive to distance changes. Energy transfer is said to occur with detectable efficiency in the 1-10 nm distance range, but is typically 4-6 nm for favorable pairs of donor and acceptor.

Radiationless energy transfer is based on the biophysical properties of fluorophores. These principles are reviewed elsewhere (Lakowicz, 1983, Principles of Fluorescence Spectroscopy, Plenum Press, New York; Jovin and Jovin, 1989, Cell Structure and Function by Microspectrofluorometry, eds. E. Kohen and J. G. Hirschberg, Academic Press, both of which are incorporated herein by reference). Briefly, a fluorophore absorbs light energy at a characteristic wavelength. This wavelength is also known as the excitation wavelength. The energy absorbed by a fluorochrome is subsequently released through various pathways, one being emission of photons to produce fluorescence. The wavelength of light being emitted is known as the emission wavelength and is an inherent characteristic of a particular fluorophore. Radiationless energy transfer is the quantum-mechanical process by which the energy of the excited state of one fluorophore is transferred without actual photon emission to a second fluorophore. That energy may then be subsequently released at the emission wavelength of the second fluorophore. The first fluorophore is generally termed the donor (D) and has an excited state of higher energy than that of the second fluorophore, termed the acceptor (A). The essential features of the process are that the emission spectrum of the donor overlap with the excitation spectrum of the acceptor, and that the donor and acceptor be sufficiently close. The distance over which radiationless energy transfer is effective depends on many factors including the fluorescence quantum efficiency of the donor, the extinction coefficient of the acceptor, the degree of overlap of their respective spectra, the refractive index of the medium, and the relative orientation of the transition moments of the two fluorophores. In addition to having an optimum emission range overlapping the excitation wavelength of the other fluorophore, the distance between D and A must be sufficiently small to allow the radiationless transfer of energy between the fluorophores.

FRET may be performed either in vivo or in vitro. Proteins are labeled either in vivo or in vitro by methods known in the art. According to the invention, a natural binding domain, sequence or polypeptide and its binding partner, comprised either by the same or by different polypeptide molecules, are differentially labeled, one with a donor and the other with an acceptor, and differences in fluorescence between a test assay, comprising a protein modifying enzyme, and a control, in which the modifying enzyme is absent, are measured using a fluorimeter or laser-scanning microscope. It will be apparent to those skilled in the art that excitation/detection means can be augmented by the incorporation of photomultiplier means to enhance detection sensitivity. The differential labels may comprise either two different fluorescent labels (e.g., fluorescent proteins as described below or the fluorophores rhodamine, fluorescein, SPQ, and others as are known in the art) or a fluorescent label and a molecule known to quench its signal; differences in the proximity of the natural binding domain, sequence or polypeptide with its binding partner with and without the protein-modifying enzyme can be gauged based upon a difference in the fluorescence spectrum or intensity observed.

This combination of protein-labeling methods and devices confers a distinct advantage over prior art methods for determining the activity of protein-modifying enzymes, as described above, in that results of all measurements are observed in real time (i.e., as a reaction progresses). This is significantly advantageous, as it allows both for rapid data collection and yields information regarding reaction kinetics under various conditions.

A sample, whether in vitro or in vivo, assayed according to the invention therefore comprises a mixture at equilibrium of the labeled natural binding domain, sequence or polypeptide and its binding partner which, when disassociated from one another, fluoresce at one frequency and, when complexed together, fluoresce at another frequency or, alternatively, of molecules which either do or do not fluoresce or show reduced fluorescence, depending upon whether or not they are associated.

The natural binding domain, sequence or polypeptide is modified to allow the attachment of a fluorescent label to the surface of that molecule or is fused in-frame with a fluorescent protein, as described below. The choice of fluorescent label will be such that upon excitation with light, labeled peptides which are associated will show optimal energy transfer between fluorophores. In the presence of a protein kinase or phosphatase, the natural binding domain, sequence or polypeptide and its binding partner dissociate due to a structural or electrostatic change which occurs as a consequence of addition or removal of a phosphate to/from the enzyme recognition site, thereby leading to a decrease in energy transfer and increased emission of light by the donor fluorophore. In this way, the state of polypeptide phosphorylation can be monitored and quantitated in real-time.

As used herein, the terms "fluorophore" and "fluorochrome" refer interchangeably to a molecule which is capable of absorbing energy at a wavelength range and releasing energy at a wavelength range other than the absorbance range. The term "excitation wavelength" refers to the range of wavelengths at which a fluorophore absorbs energy. The term "emission wavelength" refers to the range of wavelength that the fluorophore releases energy or fluoresces.

A non-limiting list of chemical fluorophores of use in the invention, along with their excitation and emission wavelengths, is presented in Table 1.

TABLE 1

| Fluorophore | Excitation (nm) | Emission (nm) | Color |
|---|---|---|---|
| PKH2 | 490 | 504 | green |
| PKH67 | 490 | 502 | green |
| Fluorescein (FITC) | 495 | 525 | green |
| Hoechst 33258 | 360 | 470 | blue |
| R-Phycoerythrin (PE) | 488 | 578 | orange-red |
| Rhodamine (TRITC) | 552 | 570 | red |
| Quantum Red .TM. | 488 | 670 | red |
| PKH26 | 551 | 567 | red |
| Texas Red | 596 | 620 | red |
| Cy3 | 552 | 570 | red |

Examples of fluorescent proteins which vary among themselves in excitation and emission maxima are as follows. These (each followed by [excitation max./emission max.] wavelengths expressed in nanometers) include wild-type Green Fluorescent Protein [395(475)/508] and the cloned mutant of Green Fluorescent Protein variants P4 [383/447], P4-3 [381/445], W7 [433(453)/475(501)], W2 [432(453)/480], S65T [489/511], P4-1 [504(396)/480],S65A[471/504], S65C [479/507], S65L [484/510], Y66F [360/442], Y66W [458/480], I0c [513/527], W1B [432(453)/476(503)], Emerald [487/508] and Sapphire [395/511]. This list is not exhaustive of fluorescent proteins known in the art; additional examples are found in the Genbank and SwissProt public databases. A number of parameters of fluorescence output are envisaged including: measuring fluorescence emitted at the emission wavelength of the acceptor (A) and donor (D) and determining the extent of energy transfer by the ratio of their emission amplitudes; measuring the fluorescence lifetime of D; measuring the rate of photobleaching of D; measuring the anisotropy of D and/or A; or measuring the Stokes shift monomer; excimer fluorescence.

Alternative Fluorescent Techniques—Monitoring Protein: Protein Binding: One embodiment of the technology can utilize monomer: excimer fluorescence as the output. The fluorophore pyrene when present as a single copy displays fluorescent emission of a particular wavelength significantly shorter than when two copies of pyrene form a planar dimer (excimer), as depicted. As above, excitation at a single wavelength (probably 340 nm) is used to review the excimer fluorescence (about 470 nm) over monomer fluorescence (about 375 nm) to quantify assembly: disassembly of the reporter molecule.

Additional embodiments of the present invention are not dependent on FRET. For example the invention can make use of fluorescence correlation spectroscopy (FCS), which relies on the measurement of the rate of diffusion of a label (see Elson and Magde, 1974 *Biopolymers,* 13: 1-27; Rigler et al., 1992, in Fluorescence Spectroscopy: New Methods an Applications, Springer Verlag, pp. 13-24; Eigen and Rigler, 1994, *Proc. Natl. Acad. Sci. U.S.A.,* 91: 5740-5747; Kinjo and Rigler, 1995, *Nucleic Acids Res.,* 23: 1795-1799).

In FCS, a focused laser beam illuminates a very small volume of solution, of the order of $10^{-15}$ liter, which at any given point in time contains only one molecule of the many under analysis. The diffusion of single molecules through the illuminated volume, over time, results in bursts of fluorescent light as the labels of the molecules are excited by the laser. Each individual burst, resulting from a single molecule, can be registered.

A labeled polypeptide will diffuse at a slower rate if it is large than if it is small. Thus, multimerized polypeptides will display slow diffusion rates, resulting in a lower number of fluorescent bursts in any given timeframe, while labeled polypeptides which are not multimerized or which have dissociated from a multimer will diffuse more rapidly. Binding of polypeptides according to the invention can be calculated directly from the diffusion rates through the illuminated volume.

Where FCS is employed, rather than FRET, it is not necessary to label more than one polypeptide. Preferably, a single polypeptide member of the multimer is labeled. The labeled polypeptide dissociates from the multimer as a result of modification, thus altering the FCS reading for the fluorescent label.

A further detection technique which may be employed in the method of the present invention is the measurement of time-dependent decay of fluorescence anisotropy. This is described, for example, in Lacowicz, 1983, Principles of Fluorescence Spectroscopy, Plenum Press, New York, incorporated herein by reference (see, for example, page 167).

Fluorescence anisotropy relies on the measurement of the rotation of fluorescent groups. Larger multimers of polypeptides rotate more slowly than monomers, allowing the formation of multimers to be monitored.

Non-fluorescent Detection Methods for Use in the Invention

The invention may be configured to exploit a number of non-fluorescent labels. In a first embodiment, the natural binding domain and binding partner therefor form, when bound, an active enzyme which is capable of participating in an enzyme-substrate reaction which has a detectable endpoint. The enzyme may comprise two or more polypeptide chains or regions of a single chain, such that upon binding of the natural binding domain to the binding partner, which are present either on two different polypeptide chains or in two different regions of a single polypeptide, these components assemble to form a functional enzyme. Enzyme function may be assessed by a number of methods, including scintillation counting and photospectroscopy. In a further embodiment, the invention may be configured such that the label is a redox enzyme, for example glucose oxidase, and the signal generated by the label is an electrical signal.

Phosphorylation of the natural binding domain and, optionally, its binding partner according to the invention is required to inhibit binding and, consequently, enzyme component assembly, thus reducing enzyme activity.

In another assay format, an enzyme is used together with a modulator of enzyme activity, such as an inhibitor or a cofactor. In such an assay, one of the enzyme and the inhibitor or cofactor is an natural binding domain, the other its binding partner. Binding of the enzyme to its inhibitor or cofactor results in modulation of enzymatic activity, which is detectable by conventional means (such as monitoring for the conversion of substrate to product for a given enzyme).

Fluorescent Protein Labels

In a FRET assay of the invention, the fluorescent protein labels are chosen such that the excitation spectrum of one of the labels (the acceptor) overlaps with the emission spectrum of the excited fluorescent label (the donor). The donor label is excited by light of appropriate intensity within the donor's excitation spectrum. The donor then emits some of the absorbed energy as fluorescent light and dissipates some of the energy by FRET to the acceptor fluorescent label. The fluorescent energy it produces is quenched by the acceptor fluorescent protein label. FRET can be manifested as a reduction in the intensity of the fluorescent signal from the donor, reduction in the lifetime of its excited state, and re-emission of fluorescent light at the longer wavelengths (lower energies) characteristic of the acceptor. When the donor and acceptor labels become spatially separated, FRET is diminished or eliminated.

One can take advantage of the FRET exhibited by a natural binding domain, sequence or polypeptide and its binding partner labeled with different fluorescent proteins, wherein one is linked to a donor and the other to an acceptor fluorescent protein, in monitoring protein phosphorylation according to the present invention. A single polypeptide may comprise a blue fluorescent protein donor and a green fluorescent protein acceptor, wherein each is fused to a different assay component (i.e., in which one is fused to the natural binding domain, sequence or polypeptide and the other to its binding partner); such a construct is herein referred to as a "tandem" fusion protein. Alternatively, two distinct polypeptides ("single" fusion proteins) one comprising a natural binding domain, sequence or polypeptide and the other its binding partner may be differentially labeled with the donor and acceptor fluorescent proteins, respectively. The construction and use of tandem fusion proteins in the invention can reduce significantly the molar concentration of peptides necessary to effect an association between differentially-labeled polypeptide assay components relative to that required when single fusion proteins are instead used. The labeled natural binding domain, sequence or polypeptide and/or its binding partner may be produced via the expression of recombinant nucleic acid molecules comprising an in-frame fusion of sequences encoding a such a polypeptide and a fluorescent protein label either in vitro (e.g., using a cell-free transcription/translation system, as described below, or instead using cultured cells transformed or transfected using methods well known in the art) or in vivo, for example in a transgenic animal including, but not limited to, insects, amphibians and mammals. A recombinant nucleic acid molecule of use in the invention may be constructed and expressed by molecular methods well known in the art, and may additionally comprise sequences including, but not limited to, those which encode a tag (e.g., a histidine tag) to enable easy purification, a secretion signal, a nuclear localization signal or other primary sequence signal capable of targeting the construct to a particular cellular location, if it is so desired.

The means by which a natural binding domain, sequence or polypeptide and its binding partner are assayed for association using fluorescent protein labels according to the invention may be briefly summarized as follows: whether or not the natural binding domain, sequence or polypeptide and its binding partner are present on a single polypeptide molecule, one is labeled with a green fluorescent protein, while the other is preferably labeled with a red or, alternatively, a blue fluorescent protein. Useful donor: acceptor pairs of fluorescent proteins (see Tsien et al., 1997, supra) include, but are not limited to: Donor: S72A, K79R, Y145F, M153A and T203I (excitation $\lambda_{395}$ nm; emission $\lambda_{511}$). Acceptor: S65G, S72A, K79R and T203Y (excitation $\lambda_{514}$ nm; emission $\lambda_{527}$ nm), or T203Y/S65G, V68L, Q69K or S72A (excitation $\lambda_{515}$ nm; emission $\lambda_{527}$ nm).

An example of a blue: green pairing is P4-3 as the donor label and S65C as the acceptor label. The natural binding domain, sequence or polypeptide and corresponding binding partner are exposed to light at, for example, 368 nm, a wavelength that is near the excitation maximum of P4-3. This wavelength excites S65C only minimally. Upon excitation, some portion of the energy absorbed by the blue fluorescent protein donor is transferred to the acceptor through FRET if the natural binding domain, sequence or polypeptide and its binding partner are in close association. As a result of this quenching, the blue fluorescent light emitted by the blue fluorescent protein is less bright than would be expected if the blue fluorescent protein existed in isolation. The acceptor (S65C) may re-emit the energy at longer wavelength, in this case, green fluorescent light.

After phosphorylation or dephosphorylation of one or both of the natural binding domain, sequence or polypeptide and its binding partner by an kinase or phosphatase, respectively, the natural binding domain, sequence or polypeptide and its binding partner (and, hence, the green and red or, less preferably, green and blue fluorescent proteins) physically separate or associate accordingly inhibiting or promoting FRET. For example, if activity of the modifying enzyme results in dissociation of a protein: protein dimer, the intensity of visible blue fluorescent light emitted by the blue fluorescent protein increases, while the intensity of visible green light emitted by the green fluorescent protein as a result of FRET, decreases.

Such a system is useful to monitor the activity of enzymes that phosphorylate or dephosphorylate the phosphorylation site of a natural binding domain, sequence or polypeptide and, optionally, its binding partner to which the fluorescent protein labels are fused, as well as the activity of kinases or phosphatases or candidate modulators of those enzymes.

In particular, this invention contemplates assays in which the amount, or, activity of a modifying enzyme in a sample is determined by contacting the sample with a natural binding domain, sequence or polypeptide and its binding partner, differentially-labeled with fluorescent proteins, as described above, and measuring changes in fluorescence of the donor label, the acceptor label or the relative fluorescence of both. Fusion proteins, as described above, which comprise either one or both of the labeled natural binding domain, sequence or polypeptide and its binding partner of an assay of the invention can be used for, among other things, monitoring the activity of a protein kinase or phosphatase inside the cell that expresses the recombinant tandem construct or two different recombinant constructs.

Advantages of single and tandem fluorescent protein/polypeptides comprising a natural binding domain, sequence or polypeptide fused to a fluorescent protein include the potential to express the natural binding domain, sequence or polypeptide in the cell (providing a convenient experimental format), the greater extinction coefficient and quantum yield of many of these proteins compared with those of the Edans fluorophore. Also, the acceptor in such a construct or pair of constructs is, itself, a fluorophore rather than a non-fluorescent quencher like Dabcyl. Alternatively, in single-label assays of the invention, whether involving use of a chemical fluorophore or a single fluorescent fusion construct, such a non-fluorescent quencher may be used. Thus, the enzyme's substrate (i.e., the natural binding domain and, optionally, the corresponding binding partner), and reaction products (i.e., the natural binding domain and, optionally, the corresponding binding partner after modification) are both fluorescent but with different fluorescent characteristics.

In particular, the substrate and modified products exhibit different ratios between the amount of light emitted by the donor and acceptor labels. Therefore, the ratio between the two fluorescence's measures the degree of conversion of substrate to products, independent of the absolute amount of either, the optical thickness of the sample, the brightness of the excitation lamp, the sensitivity of the detector, etc. Furthermore, Aequorea-derived or -related fluorescent protein labels tend to be protease resistant. Therefore, they are likely to retain their fluorescent properties throughout the course of an experiment.

Membrane Binding Assay Using Human CB1 or CB2

Cloning of the Rats Cannabinoid Receptor CB1: total RNA from rat brain (the tissue is taken from freshly killed animals and shock-frozen in liquid nitrogen) is isolated by means of acidic guanidinium thiocyanate/phenol/chloroform extraction (*J. Biol. Chem.* 1979, 18, 5294) and converted into cDNA by means of reverse transcriptase and random primers (in each case from Invitrogen). The polymerase chain reaction is carried out in a Perkin Elmer thermocycler using the enzyme Taq polymerase (Perkin Elmer); the oligonucleotide primers employed (bases 99 to 122: 5'→3', "down"; 1556-1575; 3'→5', "up") can be derived from the published sequence of the rat cannabinoid receptor (*Nature* 1990, 346, 561) and are synthesized on a DNA synthesizer, model 1380 from Applied Biosystems. One part of the PCR reaction is separated in a 1% strength agarose gel in 1×TBE buffer and then stained with ethidium bromide, only one band having the expected length being visible (approximately 1.5 kb). This PCR product was subcloned in the TA cloning vector (Invitrogen) and the nucleotide sequence of the insert is determined with T7 DNA polymerase (Sequenase, USA/Amersham) by the dideoxynucleotide chain termination reaction. The insert has a length of 1477 base pairs and contains an open reading frame of 1419 base pairs which corresponds to a protein of 473 amino acids. Computer analyses are carried out with the aid of, for example, the GCG software suite (Genetic Computer Group). The cDNA insert is subcloned in an expression vector, e.g. pRc/CMV (Invitrogen) after partial digestion with HindIII and NotI (Biolabs). This construct (plasmid CMV-RH) is employed for transfection experiments.

Stable Transfection of the CHOluc9 Reporter Cells: CHOluc9 cells are cultured in 50% Dulbecco's modified Eagle Medium/50% F-12 (DMEM/F12) which contain 10% fetal calf serum (FCS). Transfections were prepared in 6-well plates. 7.5 μg of Qiagen-purified CMV-RH plasmid DNA are added per $10^5$ cells with the DOTAP transfections system, corresponding to the experimental protocol of the manufacturer (Boehringer Mannheim). Transfected cells are selected with 1 mg/ml G418 and individual clones are obtained by limiting dilution on 96-well plates. Cell lines which express the cannabinoid receptor are identified in the presence of forskolin for the inhibition of reporter gene expression after incubation with the cannabinoid receptor agonist, WIN-55, 2121-2. Several stably transfected and subcloned cell lines are further characterized by means of RT-PCR, as described supra.

Test Optimization and Pharmacological Characterization of the CHOCB1 Reporter Cell Line: with the aim of high sensitivity and reproducibility, low variance and good suitability for carrying out on the robotic system, the luciferase test is optimized by variation of several test parameters, such as, for example, cell density, duration of the growth phase and the test incubation, forskolin concentration, medium composition. The following test protocol can be used for pharmacological characterization of the cells and for robot-assisted substance screening: the stock cultures were cultured in 50% Dulbecco's modified Eagle Medium/50% F-12 (DMEM/F12) with 10% FCS at 37° C. under 10% $CO_2$ and in each case split 1:10 after 2 to 3 days. Test cultures are inoculated into 96-well plates at 5000 cells per well and cultured at 37° C. for 70 hours. The cultures are then carefully washed with phosphate-buffered saline and reconstituted using serum-free Ultra-CHO medium (Bio-Whittaker). The substances dissolved in DMSO are diluted 1X in medium and pipetted into the test cultures (maximum DMSO final concentration in the test mixture: 0.5%). 20 minutes later, forskolin is added and the cultures are then incubated at 37° C. in an incubator for 3 hours. The supernatants are then removed and the cells are lysed by addition of 25 μl of lysis reagent (25 mM triphosphate, pH 7.8 with 2 mM DTT, 10% glycerol, 3% TritonX100). Directly after this, luciferase substrate solution (2.5 mM ATP, 0.5 mM luciferin, 0.1 mM coenzyme A, 10 mM tricine, 1.35 mM $MgSO_4$, 15 mM DTT, pH 7.8) is added, the mixture was briefly shaken, and the luciferase activity is measured using a Hamamatzu camera system. For inactivation of $G_i$ proteins, the test cultures were treated with 5 ng/ml (final conc.) of pertussis toxin for 16 hours before the test. The $IC_{50}$ values are calculated using the Graph Pad Prism program (Hill equation, specific: one-site competition).

Binding Studies on Cortex Membranes: membrane protein is prepared from different tissues or from cells by standard methods. Buffer, labeled ligands, DMSO or test substance are pipetted together, then 100 μg of protein are added, and the mixture is well mixed and incubated in a water bath at 30° C.

for 60 min. After expiration of the incubation time, the reaction is stopped by addition of ice-cold incubation buffer to each tube. After filtering off, washing is carried out with ¾ ml of incubation buffer. The filters are transferred to minivials and the radioactivity is determined in a liquid scintillation counter.

Inhibition of Glutamate Release: after decapitation of a rat, the skull is opened, and the brain is lifted out and cut through along the median fissure. The hippocampus is exposed, separated from the remaining tissue, cut into 350 µm thick sections and incubated at 37° C. in straining vessels for 60 min. Followed by basal value and stimulation 1 with 75 mM KCl (S 1), the sections are incubated with test substance and then the stimulation with KCl and test substance (S2) is repeated. The glutamate concentration of the samples to be investigated is then measured by means of an enzymatic reaction (GLDH) and fluorometric measurement of NADH. By means of a calibration curve, the glutamate content of the sample is determined, and with knowledge of the protein content the glutamate content/mg of protein can be calculated. The ratio S2/S1 is compared; glutamate release inhibitors reduce this ratio in a concentration-dependent manner.

Biomarkers and Traumatic Brain Injury

The invention provides the step of correlating the presence or amount of one or more neural protein(s) with the severity and/or type of nerve cell injury. The amount of a neural proteins, peptides, fragments, derivatives or the modified forms, thereof, directly relates to severity of nerve tissue injury as more severe injury damages a greater number of nerve cells which in turn causes a larger amount of neural protein(s) to accumulate in the biological sample (e.g., CSF). Whether a nerve cell injury triggers an apoptotic, oncotic (necrotic) or type 2 (autophagic) cell death, can be determined by examining the unique proteins released into the biofluid in response to different cell death phenotype. The unique proteins are detected from the many cell types that comprise the nervous system. For example, astroglia, oligodendrocytes, microglia cells, Schwann cells, fibroblast, neuroblast, neural stem cells and mature neurons. Furthermore, mature neurons are differentiated into dedicated subtype fusing a primary neural transmitter such as cholinergic (nicotinic and mucarinic), glutamatergic, gabaergic, serotonergic, dopaminergic. Each of this neuronal subtype express unique neural proteins such as those dedicated for the synthesis, metabolism and transporter and receptor of each unique neurotransmitter system. Lastly, within a single nerve cell, there are subcellularly defined structures matched with unique neural proteins (dendritic, axonal, myelin sheath, presynaptic terminal and postsynaptic density). By monitoring the release of proteins unique to each of these regions, subcellular damage can be monitored and defined after brain injury.

The biomarkers of the invention can be detected in a sample by any means. Methods for detecting the biomarkers are described in detail in the materials and methods and Examples which follow. For example, immunoassays, include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, fluorescent immunoassays and the like. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding an antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody to immunoprecipitate a particular antigen can be assessed by, e.g., Western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen (i.e. neural biomarker), coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

Identification of New Markers

In a preferred embodiment, a biological sample is obtained from a patient with neural injury, TBI, subarachnoid hemorrhage, epilepsy, stroke, and other forms of brain injury. Biological samples comprising biomarkers from other patients and control subjects (i.e. normal healthy individuals of similar age, sex, physical condition) are used as comparisons. Biological samples are extracted as discussed above. Preferably, the sample is prepared prior to detection of biomarkers. Typically, preparation involves fractionation of the sample and collection of fractions determined to contain the biomarkers. Methods of pre-fractionation include, for example, size exclusion chromatography, ion exchange chromatography, heparin chromatography, affinity chromatography, sequential extraction, gel electrophoresis and liquid chromatography. The analytes also may be modified prior to detection. These methods are useful to simplify the sample for further analysis. For example, it can be useful to remove high abundance proteins, such as albumin, from blood before analysis.

In one embodiment, a sample can be pre-fractionated according to size of proteins in a sample using size exclusion chromatography. For a biological sample wherein the amount of sample available is small, preferably a size selection spin column is used. In general, the first fraction that is eluted from the column ("fraction 1") has the highest percentage of high molecular weight proteins; fraction 2 has a lower percentage of high molecular weight proteins; fraction 3 has even a lower percentage of high molecular weight proteins; fraction 4 has the lowest amount of large proteins; and so on. Each fraction can then be analyzed by immunoassays, gas phase ion spectrometry, and the like, for the detection of markers.

In another embodiment, a sample can be pre-fractionated by anion exchange chromatography. Anion exchange chromatography allows pre-fractionation of the proteins in a sample roughly according to their charge characteristics. For example, a Q anion-exchange resin can be used (e.g., Q HyperD F, Biosepra), and a sample can be sequentially eluted with eluants having different pH's. Anion exchange chromatography allows separation of biomarkers in a sample that are more negatively charged from other types of biomarkers. Proteins that are eluted with an eluant having a high pH is likely to be weakly negatively charged, and a fraction that is eluted with an eluant having a low pH is likely to be strongly negatively charged. Thus, in addition to reducing complexity of a sample, anion exchange chromatography separates proteins according to their binding characteristics.

In yet another embodiment, a sample can be pre-fractionated by heparin chromatography. Heparin chromatography allows pre-fractionation of the markers in a sample also on the basis of affinity interaction with heparin and charge characteristics. Heparin, a sulfated mucopolysaccharide, will bind markers with positively charged moieties and a sample can be sequentially eluted with eluants having different pH's or salt concentrations. Markers eluted with an eluant having a low pH are more likely to be weakly positively charged. Markers eluted with an eluant having a high pH are more likely to be strongly positively charged. Thus, heparin chromatography also reduces the complexity of a sample and separates markers according to their binding characteristics.

In yet another embodiment, a sample can be pre-fractionated by isolating proteins that have a specific characteristic, e.g. are glycosylated. For example, a CSF sample can be fractionated by passing the sample over a lectin chromatography column (which has a high affinity for sugars). Glycosylated proteins will bind to the lectin column and non-glycosylated proteins will pass through the flow through. Glycosylated proteins are then eluted from the lectin column with an eluant containing a sugar, e.g., N-acetyl-glucosamine and are available for further analysis.

Thus there are many ways to reduce the complexity of a sample based on the binding properties of the proteins in the sample, or the characteristics of the proteins in the sample.

In yet another embodiment, a sample can be fractionated using a sequential extraction protocol. In sequential extraction, a sample is exposed to a series of adsorbents to extract different types of biomarkers from a sample. For example, a sample is applied to a first adsorbent to extract certain proteins, and an eluant containing non-adsorbent proteins (i.e., proteins that did not bind to the first adsorbent) is collected. Then, the fraction is exposed to a second adsorbent. This further extracts various proteins from the fraction. This second fraction is then exposed to a third adsorbent, and so on.

Any suitable materials and methods can be used to perform sequential extraction of a sample. For example, a series of spin columns comprising different adsorbents can be used. In another example, a multi-well comprising different adsorbents at its bottom can be used. In another example, sequential extraction can be performed on a probe adapted for use in a gas phase ion spectrometer, wherein the probe surface comprises adsorbents for binding biomarkers. In this embodiment, the sample is applied to a first adsorbent on the probe, which is subsequently washed with an eluant. Markers that do not bind to the first adsorbent are removed with an eluant. The markers that are in the fraction can be applied to a second adsorbent on the probe, and so forth. The advantage of performing sequential extraction on a gas phase ion spectrometer probe is that markers that bind to various adsorbents at every stage of the sequential extraction protocol can be analyzed directly using a gas phase ion spectrometer.

In yet another embodiment, biomarkers in a sample can be separated by high-resolution electrophoresis, e.g., one or two-dimensional gel electrophoresis. A fraction containing a marker can be isolated and further analyzed by gas phase ion spectrometry. Preferably, two-dimensional gel electrophoresis is used to generate two-dimensional array of spots of biomarkers, including one or more markers. See, e.g., Jungblut and Thiede, *Mass Spectr. Rev.* 16:145-162 (1997).

The two-dimensional gel electrophoresis can be performed using methods known in the art. See, e.g., Deutscher ed., Methods In Enzymology vol. 182. Typically, biomarkers in a sample are separated by, e.g., isoelectric focusing, during which biomarkers in a sample are separated in a pH gradient until they reach a spot where their net charge is zero (i.e., isoelectric point). This first separation step results in one-dimensional array of biomarkers. The biomarkers in one dimensional array is further separated using a technique generally distinct from that used in the first separation step. For example, in the second dimension, biomarkers separated by isoelectric focusing are further separated using a polyacrylamide gel, such as polyacrylamide gel electrophoresis in the presence of sodium dodecyl sulfate (SDS-PAGE). SDS-PAGE gel allows further separation based on molecular mass of biomarkers. Typically, two-dimensional gel electrophoresis can separate chemically different biomarkers in the molecular mass range from 1000-200,000 Da within complex mixtures.

Biomarkers in the two-dimensional array can be detected using any suitable methods known in the art. For example, biomarkers in a gel can be labeled or stained (e.g., Coomassie Blue or silver staining). If gel electrophoresis generates spots that correspond to the molecular weight of one or more markers of the invention, the spot can be further analyzed by densitometric analysis or gas phase ion spectrometry. For example, spots can be excised from the gel and analyzed by gas phase ion spectrometry. Alternatively, the gel containing biomarkers can be transferred to an inert membrane by applying an electric field. Then a spot on the membrane that approximately corresponds to the molecular weight of a marker can be analyzed by gas phase ion spectrometry. In gas phase ion spectrometry, the spots can be analyzed using any suitable techniques, such as MALDI or SELDI.

Prior to gas phase ion spectrometry analysis, it may be desirable to cleave biomarkers in the spot into smaller fragments using cleaving reagents, such as proteases (e.g., trypsin). The digestion of biomarkers into small fragments provides a mass fingerprint of the biomarkers in the spot, which can be used to determine the identity of markers if desired.

In yet another embodiment, high performance liquid chromatography (HPLC) can be used to separate a mixture of biomarkers in a sample based on their different physical properties, such as polarity, charge and size. HPLC instruments typically consist of a reservoir of mobile phase, a pump, an injector, a separation column, and a detector. Biomarkers in a sample are separated by injecting an aliquot of the sample onto the column. Different biomarkers in the mixture pass through the column at different rates due to differences in their partitioning behavior between the mobile liquid phase and the stationary phase. A fraction that corresponds to the molecular weight and/or physical properties of one or more markers can be collected. The fraction can then be analyzed by gas phase ion spectrometry to detect markers.

Optionally, a marker can be modified before analysis to improve its resolution or to determine its identity. For example, the markers may be subject to proteolytic digestion before analysis. Any protease can be used. Proteases, such as trypsin, that are likely to cleave the markers into a discrete number of fragments are particularly useful. The fragments that result from digestion function as a fingerprint for the markers, thereby enabling their detection indirectly. This is particularly useful where there are markers with similar molecular masses that might be confused for the marker in question. Also, proteolytic fragmentation is useful for high molecular weight markers because small markers are more easily resolved by mass spectrometry. In another example, biomarkers can be modified to improve detection resolution. For instance, neuraminidase can be used to remove terminal sialic acid residues from glycoproteins to improve binding to an anionic adsorbent and to improve detection resolution. In another example, the markers can be modified by the attachment of a tag of particular molecular weight that specifically bind to molecular markers, further distinguishing them. Optionally, after detecting such modified markers, the identity of the markers can be further determined by matching the physical and chemical characteristics of the modified markers in a protein database (e.g., SwissProt).

After preparation, biomarkers in a sample are typically captured on a substrate for detection. Traditional substrates include antibody-coated 96-well plates or nitrocellulose membranes that are subsequently probed for the presence of proteins. Preferably, the biomarkers are identified using immunoassays as described above. However, preferred methods also include the use of biochips. Preferably the biochips are protein biochips for capture and detection of proteins. Many protein biochips are described in the art. These include, for example, protein biochips produced by Packard BioScience Company (Meriden CT), Zyomyx (Hayward, Calif.) and Phylos (Lexington, Mass.). In general, protein biochips comprise a substrate having a surface. A capture reagent or adsorbent is attached to the surface of the substrate. Frequently, the surface comprises a plurality of addressable locations, each of which location has the capture reagent bound there. The capture reagent can be a biological molecule, such as a polypeptide or a nucleic acid, which captures other biomarkers in a specific manner. Alternatively, the capture reagent can be a chromatographic material, such as an anion exchange material or a hydrophilic material. Examples of such protein biochips are described in the following patents or patent applications: U.S. Pat. No. 6,225,047 (Hutchens and Yip, "Use of retentate chromatography to generate difference maps," May 1, 2001), International publication WO 99/51773 (Kuimelis and Wagner, "Addressable protein arrays," Oct. 14, 1999), International publication WO 00/04389 (Wagner et al., "Arrays of protein-capture agents and methods of use thereof," Jul. 27, 2000), International publication WO 00/56934 (Englert et al., "Continuous porous matrix arrays," Sep. 28, 2000).

In general, a sample containing the biomarkers is placed on the active surface of a biochip for a sufficient time to allow binding. Then, unbound molecules are washed from the surface using a suitable eluant. In general, the more stringent the eluant, the more tightly the proteins must be bound to be retained after the wash. The retained protein biomarkers now can be detected by appropriate means.

Analytes captured on the surface of a protein biochip can be detected by any method SELDI mass spectrometry, is a particularly useful method for detection of the biomarkers of this invention.

Preferably, a laser desorption time-of-flight mass spectrometer is used in embodiments of the invention. In laser desorption mass spectrometry, a substrate or a probe comprising markers is introduced into an inlet system. The markers are desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of markers of specific mass to charge ratio.

Matrix-assisted laser desorption/ionization mass spectrometry, or MALDI-MS, is a method of mass spectrometry that involves the use of an energy absorbing molecule, frequently called a matrix, for desorbing proteins intact from a probe surface. MALDI is described, for example, in U.S. Pat. No. 5,118,937 (Hillenkamp et al.) and U.S. Pat. No. 5,045,694 (Beavis and Chait). In MALDI-MS the sample is typically mixed with a matrix material and placed on the surface of an inert probe. Exemplary energy absorbing molecules include cinnamic acid derivatives, sinapinic acid ("SPA"), cyano hydroxy cinnamic acid ("CHCA") and dihydroxybenzoic acid. Other suitable energy absorbing molecules are known to those skilled in this art. The matrix dries, forming crystals that encapsulate the analyte molecules. Then the analyte molecules are detected by laser desorption/ionization mass spectrometry. MALDI-MS is useful for detecting the biomarkers of this invention if the complexity of a sample has been substantially reduced using the preparation methods described above.

Surface-enhanced laser desorption/ionization mass spectrometry, or SELDI-MS represents an improvement over MALDI for the fractionation and detection of biomolecules, such as proteins, in complex mixtures. SELDI is a method of mass spectrometry in which biomolecules, such as proteins, are captured on the surface of a protein biochip using capture reagents that are bound there. Typically, non-bound molecules are washed from the probe surface before interrogation. SELDI is described, for example, in: U.S. Pat. No. 5,719,060 ("Method and Apparatus for Desorption and Ionization of Analytes," Hutchens and Yip, Feb. 17, 1998,) U.S. Pat. No. 6,225,047 ("Use of Retentate Chromatography to Generate Difference Maps," Hutchens and Yip, May 1, 2001) and Weinberger et al., "Time-of-flight mass spectrometry," in Encyclopedia of Analytical Chemistry, R. A. Meyers, ed., pp 11915-11918 John Wiley & Sons Chichesher, 2000.

Markers on the substrate surface can be desorbed and ionized using gas phase ion spectrometry. Any suitable gas phase ion spectrometers can be used as long as it allows markers on the substrate to be resolved. Preferably, gas phase ion spectrometers allow quantitation of markers.

In one embodiment, a gas phase ion spectrometer is a mass spectrometer. In a typical mass spectrometer, a substrate or a probe comprising markers on its surface is introduced into an inlet system of the mass spectrometer. The markers are then desorbed by a desorption source such as a laser, fast atom bombardment, high energy plasma, electrospray ionization, thermospray ionization, liquid secondary ion MS, field desorption, etc. The generated desorbed, volatilized species consist of preformed ions or neutrals which are ionized as a direct consequence of the desorption event. Generated ions are collected by an ion optic assembly, and then a mass analyzer disperses and analyzes the passing ions. The ions exiting the mass analyzer are detected by a detector. The detector then translates information of the detected ions into mass-to-charge ratios. Detection of the presence of markers or other substances will typically involve detection of signal intensity. This, in turn, can reflect the quantity and character of markers bound to the substrate. Any of the components of a mass spectrometer (e.g., a desorption source, a mass analyzer, a detector, etc.) can be combined with other suitable components described herein or others known in the art in embodiments of the invention.

In another embodiment, an immunoassay can be used to detect and analyze markers in a sample. This method comprises: (a) providing an antibody that specifically binds to a marker; (b) contacting a sample with the antibody; and (c) detecting the presence of a complex of the antibody bound to the marker in the sample.

To prepare an antibody that specifically binds to a marker, purified markers or their nucleic acid sequences can be used. Nucleic acid and amino acid sequences for markers can be obtained by further characterization of these markers. For example, each marker can be peptide mapped with a number of enzymes (e.g., trypsin, V8 protease, etc.). The molecular weights of digestion fragments from each marker can be used to search the databases, such as SwissProt database, for sequences that will match the molecular weights of digestion fragments generated by various enzymes. Using this method, the nucleic acid and amino acid sequences of other markers can be identified if these markers are known proteins in the databases.

Alternatively, the proteins can be sequenced using protein ladder sequencing. Protein ladders can be generated by, for example, fragmenting the molecules and subjecting fragments to enzymatic digestion or other methods that sequentially remove a single amino acid from the end of the fragment. Methods of preparing protein ladders are described, for example, in International Publication WO 93/24834 (Chait et al.) and U.S. Pat. No. 5,792,664 (Chait et al.). The ladder is then analyzed by mass spectrometry. The difference in the masses of the ladder fragments identify the amino acid removed from the end of the molecule.

If the markers are not known proteins in the databases, nucleic acid and amino acid sequences can be determined with knowledge of even a portion of the amino acid sequence of the marker. For example, degenerate probes can be made based on the N-terminal amino acid sequence of the marker. These probes can then be used to screen a genomic or cDNA library created from a sample from which a marker was initially detected. The positive clones can be identified, amplified, and their recombinant DNA sequences can be subcloned using techniques which are well known. See, e.g., Current Protocols for Molecular Biology (Ausubel et al., Green Publishing Assoc. and Wiley-Interscience 1989) and Molecular Cloning: A Laboratory Manual, 3rd Ed. (Sambrook et al., Cold Spring Harbor Laboratory, NY 2001).

Using the purified markers or their nucleic acid sequences, antibodies that specifically bind to a marker can be prepared using any suitable methods known in the art. See, e.g., Coligan, Current Protocols in Immunology (1991); Harlow & Lane, Antibodies: A Laboratory Manual (1988); Goding, Monoclonal Antibodies: Principles and Practice (2d ed. 1986); and Kohler & Milstein, Nature 256:495-497 (1975). Such techniques include, but are not limited to, antibody preparation by selection of antibodies from libraries of recombinant antibodies in phage or similar vectors, as well as preparation of polyclonal and monoclonal antibodies by immunizing rabbits or mice (see, e.g., Huse et al., Science 246:1275-1281 (1989); Ward et al., Nature 341:544-546 (1989)).

After the antibody is provided, a marker can be detected and/or quantified using any of suitable immunological binding assays known in the art (see, e.g., U.S. Pat. Nos. 4,366,241; 4,376,110; 4,517,288; and 4,837,168). Useful assays include, for example, an enzyme immune assay (EIA) such as enzyme-linked immunosorbent assay (ELISA), a radioimmune assay (RIA), a Western blot assay, or a slot blot assay. These methods are also described in, e.g., Methods in Cell Biology: Antibodies in Cell Biology, volume 37 (Asai, ed. 1993); Basic and Clinical Immunology (Stites & Terr, eds., 7th ed. 1991); and Harlow & Lane, supra.

Generally, a sample obtained from a subject can be contacted with the antibody that specifically binds the marker. Optionally, the antibody can be fixed to a solid support to facilitate washing and subsequent isolation of the complex, prior to contacting the antibody with a sample. Examples of solid supports include glass or plastic in the form of, e.g., a microtiter plate, a stick, a bead, or a microbead. Antibodies can also be attached to a probe substrate or ProteinChip® array described above. The sample is preferably a biological fluid sample taken from a subject. Examples of biological fluid samples include cerebrospinal fluid, blood, serum, plasma, neuronal cells, tissues, urine, tears, saliva etc. In a preferred embodiment, the biological fluid comprises cerebrospinal fluid. The sample can be diluted with a suitable eluant before contacting the sample to the antibody.

After incubating the sample with antibodies, the mixture is washed and the antibody-marker complex formed can be detected. This can be accomplished by incubating the washed mixture with a detection reagent. This detection reagent may be, e.g., a second antibody which is labeled with a detectable label. Exemplary detectable labels include magnetic beads (e.g., DYNABEADS™), fluorescent dyes, radiolabels, enzymes (e.g., horse radish peroxidase, alkaline phosphatase and others commonly used in an ELISA), and colorimetric labels such as colloidal gold or colored glass or plastic beads. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker is incubated simultaneously with the mixture.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations and the like. Usually the assays will be carried out at ambient temperature, although they can be conducted over a range of temperatures, such as 10° C. to 40° C.

Detection of Biomarkers

Immunoassays can be used to determine presence or absence of a marker in a sample as well as the quantity of a marker in a sample. First, a test amount of a marker in a sample can be detected using the immunoassay methods described above. If a marker is present in the sample, it will form an antibody-marker complex with an antibody that specifically binds the marker under suitable incubation conditions described above. The amount of an antibody-marker complex can be determined by comparing to a standard. A standard can be, e.g., a known compound or another protein known to be present in a sample. As noted above, the test amount of marker need not be measured in absolute units, as long as the unit of measurement can be compared to a control.

The methods for detecting these markers in a sample have many applications. For example, one or more markers can be measured to aid in the diagnosis of spinal injury, brain injury, the degree of injury, neural injury due to neuronal disorders, alcohol and drug abuse, fetal injury due to alcohol and/or drug abuse by pregnant mothers, etc. In another example, the methods for detection of the markers can be used to monitor responses in a subject to treatment. In another example, the methods for detecting markers can be used to assay for and to identify compounds that modulate expression of these markers in vivo or in vitro.

Data generated by desorption and detection of markers can be analyzed using any suitable means. In one embodiment, data is analyzed with the use of a programmable digital computer. The computer program generally contains a readable medium that stores codes. Certain code can be devoted to memory that includes the location of each feature on a probe, the identity of the adsorbent at that feature and the elution conditions used to wash the adsorbent. The computer also contains code that receives as input, data on the strength of the signal at various molecular masses received from a particular addressable location on the probe. This data can indicate the number of markers detected, including the strength of the signal generated by each marker.

Data analysis can include the steps of determining signal strength (e.g., height of peaks) of a marker detected and removing "outliers" (data deviating from a predetermined statistical distribution). The observed peaks can be normalized, a process whereby the height of each peak relative to some reference is calculated. For example, a reference can be background noise generated by instrument and chemicals (e.g., energy absorbing molecule) which is set as zero in the scale. Then the signal strength detected for each marker or other biomolecules can be displayed in the form of relative intensities in the scale desired (e.g., 100). Alternatively, a standard (e.g., a CSF protein) may be admitted with the sample so that a peak from the standard can be used as a reference to calculate relative intensities of the signals observed for each marker or other markers detected.

The computer can transform the resulting data into various formats for displaying. In one format, referred to as "spectrum view or retentate map," a standard spectral view can be displayed, wherein the view depicts the quantity of marker reaching the detector at each particular molecular weight. In another format, referred to as "peak map," only the peak height and mass information are retained from the spectrum view, yielding a cleaner image and enabling markers with nearly identical molecular weights to be more easily seen. In yet another format, referred to as "gel view," each mass from the peak view can be converted into a grayscale image based on the height of each peak, resulting in an appearance similar to bands on electrophoretic gels. In yet another format, referred to as "3-D overlays," several spectra can be overlaid to study subtle changes in relative peak heights. In yet another format, referred to as "difference map view," two or more spectra can be compared, conveniently highlighting unique markers and markers which are up- or down-regulated between samples. Marker profiles (spectra) from any two samples may be compared visually. In yet another format, Spotfire Scatter Plot can be used, wherein markers that are detected are plotted as a dot in a plot, wherein one axis of the plot represents the apparent molecular mass of the markers detected and another axis represents the signal intensity of markers detected. For each sample, markers that are detected and the amount of markers present in the sample can be saved in a computer readable medium. This data can then be compared to a control (e.g., a profile or quantity of markers detected in control, e.g., normal, healthy subjects in whom neural injury is undetectable).

Diagnosis of Traumatic Brain Injury

In another aspect, the invention provides methods for aiding a human neural injury and/or neural disorder diagnosis using one or more markers. These markers can be used singularly or in combination with other markers in any set, for example, CB1 and any neural peptide. The markers are differentially present in samples of a human patient, for example a TBI patient, subarachnoid hemorrhage, epilepsy, stroke, and other forms of brain injury, and a normal subject in whom neural injury is undetectable. For example, some of the markers are expressed at an elevated level and/or are present at a higher frequency in human patients with neural injury and/or neuronal disorders than in normal subjects. Therefore, detection of one or more of these markers in a person would provide useful information regarding the probability that the person may have neural injury such as traumatic brain injury.

Nervous system diseases, neuronal disorders, and/or conditions, (e.g. TBI, aubarachnoid hemorrhage, epilepsy, stroke, and other forms of brain injury) which can be treated, prevented, and/or diagnosed with the compositions of the invention (e.g., polypeptides, polynucleotides, and/or agonists or antagonists), include, but are not limited to, nervous system injuries, and diseases, disorders, and/or conditions which result in either a disconnection of axons, a diminution or degeneration of neurons, or demyelination. Nervous system lesions which may be treated, prevented, and/or diagnosed in a patient (including human and non-human mammalian patients) according to the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which server a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS); (6) lesions associated with nutritional diseases, disorders, and/or conditions, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

Accordingly, embodiments of the invention include methods for diagnosing brain injury and/or neuronal disorders, wherein the method comprises: (a) detecting at least one marker in a sample, wherein the marker is a cannabinoid receptor, peptides, fragments and derivatives thereof; and (b) correlating the detection of the marker or markers with a probable diagnosis of brain injury and/or neuronal disorder. The correlation may take into account the amount of the marker or markers in the sample compared to a control amount of the marker or markers (up or down regulation of the marker or markers) (e.g., in normal subjects in whom human neural injury is undetectable). The correlation may take into account the presence or absence of the markers in a test sample and the frequency of detection of the same markers in a control. The correlation may take into account both of such factors to facilitate determination of whether a subject has neural injury, the degree of severity of the neural injury, and subcellular location of the injury, or not.

Any suitable samples can be obtained from a subject to detect markers. Preferably, a sample is a cerebrospinal fluid sample from the subject. If desired, the sample can be prepared as described above to enhance detectability of the markers. For example, to increase the detectability of markers, a blood serum sample from the subject can be preferably fractionated by, e.g., Cibacron blue agarose chromatography and single stranded DNA affinity chromatography, anion exchange chromatography and the like. Sample preparations, such as pre-fractionation protocols, is optional and may not be necessary to enhance detectability of markers depending on the methods of detection used. For example, sample preparation may be unnecessary if antibodies that specifically bind markers are used to detect the presence of markers in a sample.

Any suitable method can be used to detect a marker or markers in a sample. For example, an immunoassay or gas phase ion spectrometry can be used as described above. Using these methods, one or more markers can be detected. Preferably, a sample is tested for the presence of a plurality of markers. Detecting the presence of a plurality of markers, rather than a single marker alone, would provide more information for the diagnostician. Specifically, the detection of a plurality of markers in a sample would increase the percentage of true positive and true negative diagnoses and would decrease the percentage of false positive or false negative diagnoses.

The detection of the marker or markers is then correlated with a probable diagnosis of neural injury and/or neuronal disorders. In some embodiments, the detection of the mere presence or absence of a marker, without quantifying the amount of marker, is useful and can be correlated with a probable diagnosis of neural injury and/or neuronal disorders.

In other embodiments, the detection of markers can involve quantifying the markers to correlate the detection of markers with a probable diagnosis of brain injury, degree of severity of brain injury, diagnosis of neural disorders and the like. Thus, if the amount of the markers detected in a subject being tested is higher compared to a control amount, then the subject being tested has a higher probability of having such injuries and/or neural disorders.

Similarly, in another embodiment, the detection of markers can further involve quantifying the markers to correlate the detection of markers with a probable diagnosis of neural injury, degree of severity of neural injury, diagnosis of neural disorders and the like, wherein the markers are present in lower quantities in CSF or blood serum samples from patients than in blood serum samples of normal subjects. Thus, if the amount of the markers detected in a subject being tested is lower compared to a control amount, then the subject being tested has a higher probability of having brain injury and/or neural disorder.

When the markers are quantified, it can be compared to a control. A control can be, e.g., the average or median amount of marker present in comparable samples of normal subjects in whom brain injury and/or neural disorders, is undetectable. The control amount if measured under the same or substantially similar experimental conditions as in measuring the test amount. For example, if a test sample is obtained from a subject's cerebrospinal fluid and/or blood serum sample and a marker is detected using a particular probe, then a control amount of the marker is preferably determined from a serum sample of a patient using the same probe. It is preferred that the control amount of marker is determined based upon a significant number of samples from normal subjects who do not have neural injury and/or neuronal disorders so that it reflects variations of the marker amounts in that population.

Data generated by mass spectrometry can then be analyzed by computer software. The software can comprise code that converts signal from the mass spectrometer into computer readable form. The software also can include code that applies an algorithm to the analysis of the signal to determine whether the signal represents a "peak" in the signal corresponding to a marker of this invention, or other useful markers. The software also can include code that executes an algorithm that compares signal from a test sample to a typical signal characteristic of "normal" and human neural injury and determines the closeness of fit between the two signals. The software also can include code indicating which the test sample is closest to, thereby providing a probable diagnosis.

Biomarker Specific Antibodies

Neural biomarkers obtained from samples in patients suffering from varying brain injuries, subarachnoid hemorrhage, epilepsy, stroke, and other forms of brain injury, degrees of severity of injury, neuronal disorders and the like, can be prepared as described above. Furthermore, neural biomarkers can be subjected to enzymatic digestion to obtain fragments or peptides of the biomarkers for the production of antibodies to different antigenic epitopes that can be present in a peptide versus the whole protein. Antigenic epitopes are useful, for example, to raise antibodies, including monoclonal antibodies, that specifically bind the epitope. Antigenic epitopes can be used as the target molecules in immunoassays. (See, for instance, Wilson et al., Cell 37:767-778 (1984); Sutcliffe et al., Science 219:660-666 (1983)).

Neural biomarker epitopes can be used, for example, to induce antibodies according to methods well known in the art. (See, for instance, Sutcliffe et al., supra; Wilson et al., supra; Chow et al., *Proc. Natl. Acad. Sci.* USA 82:910-914; and Bittle et al., *J. Gen. Virol.* 66:2347-2354 (1985). Neural polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., *J. Gen. Virol.*, 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 µg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Nucleic acids neural biomarker epitopes can also be recombined with a gene of interest as an epitope tag (e.g., the hemaglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto $Ni^{2+}$ nitriloacetic acid-agarose column and histidine-tagged proteins can be selectively eluted with imidazole-containing buffers.

The antibodies of the present invention may be generated by any suitable method known in the art. The antibodies of the present invention can comprise polyclonal antibodies. Methods of preparing polyclonal antibodies are known to the skilled artisan (Harlow, et al., Antibodies: A Laboratory Manual, (Cold spring Harbor Laboratory Press, 2nd ed. (1988), which is hereby incorporated herein by reference). For example, a polypeptide of the invention can be administered to various host animals including, but not limited to, rabbits, mice, rats, etc. to induce the production of sera containing polyclonal antibodies specific for the antigen. The administration of the polypeptides of the present invention may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art. For the purposes of the invention, "immunizing agent" may be defined as a polypeptide of the invention, including fragments, variants, and/or derivatives thereof, in addition to fusions with heterologous polypeptides and other forms of the polypeptides as may be described herein.

Typically, the immunizing agent and/or adjuvant will be injected in the mammal by multiple subcutaneous or intraperitoneal injections, though they may also be given intramuscularly, and/or through I.V. The immunizing agent may include polypeptides of the present invention or a fusion protein or variants thereof. Depending upon the nature of the polypeptides (i.e., percent hydrophobicity, percent hydrophilicity, stability, net charge, isoelectric point etc.), it may be useful to conjugate the immunizing agent to a protein known to be immunogenic in the mammal being immunized. Such conjugation includes either chemical conjugation by derivatizing active chemical functional groups to both the polypeptide of the present invention and the immunogenic protein such that a covalent bond is formed, or through fusion-protein based methodology, or other methods known to the skilled artisan. Examples of such immunogenic proteins include, but are not limited to keyhole limpet hemocyanin, serum albumin, bovine thyroglobulin, and soybean trypsin inhibitor. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Additional examples of adjuvants which may be employed includes the MPL-TDM adjuvant (monophosphoryl lipid A, synthetic trehalose dicorynomycolate). The immunization protocol may be selected by one skilled in the art without undue experimentation.

The antibodies of the present invention can also comprise monoclonal antibodies. Monoclonal antibodies may be prepared using hybridoma methods, such as those described by Kohler and Milstein, *Nature,* 256:495 (1975) and U.S. Pat. No. 4,376,110, by Harlow, et al., Antibodies: A Laboratory Manual, (Cold spring Harbor Laboratory Press, 2nd ed. (1988), by Hammerling, et al., Monoclonal Antibodies and T-Cell Hybridomas (Elsevier, N.Y., (1981)), or other methods known to the artisan. Other examples of methods which may be employed for producing monoclonal antibodies includes, but are not limited to, the human B-cell hybridoma technique (Kosbor et al., 1983, *Immunology Today* 4:72; Cole et al., 1983, *Proc. Natl. Acad. Sci.* USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro and in vivo. Production of high titers of mAbs in vivo makes this the presently preferred method of production.

In a hybridoma method, a mouse, a humanized mouse, a mouse with a human immune system, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include neural polypeptides, fragments or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986), pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. As inferred through the specification, human myeloma and mouse-human heteromyeloma cell lines also have been described for the production of human monoclonal antibodies (Kozbor, *J. Immunol.,* 133:3001 (1984); Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the neural polypeptides of the present invention. Preferably, the binding specificity of monoclonal antibodies produced by the hybridoma cells is determined by immunoprecipitation or by an in vitro binding assay, such as radioimmunoassay (RIA) or enzyme-linked immunoadsorbant assay (ELISA). Such techniques are known in the art and within the skill or the artisan. The binding affinity of the monoclonal antibody can, for example, be determined by the Scatchard analysis of Munson and Pollart, *Anal. Biochem.,* 107:220 (1980).

After the described hybridoma cells are identified, the clones may be subcloned by limiting dilution procedures and grown by standard methods (Goding, supra). Suitable culture media for this purpose include, for example, Dulbecco's Modified Eagle's Medium and RPMI-1640. Alternatively, the hybridoma cells may be grown in vivo as ascites in a mammal. The monoclonal antibodies secreted by the subclones may be isolated or purified from the culture medium or ascites fluid by conventional immunoglobulin purification procedures such as, for example, protein A-sepharose, hydroxyapatite chromatography, gel exclusion chromatography, gel electrophoresis, dialysis, or affinity chromatography.

The skilled artisan would acknowledge that a variety of methods exist in the art for the production of monoclonal antibodies and thus, the invention is not limited to their sole production in hybridomas. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or such chains from human, humanized, or other sources). The hybridoma cells of the invention serve as a preferred source of such DNA. Once isolated, the DNA may be placed into expression vectors, which are then transformed into host cells such as Simian COS cells, Chinese hamster ovary (CHO) cells, or myeloma cells that do not otherwise produce immunoglobulin protein, to obtain the synthesis of monoclonal antibodies in the recombinant host cells.

Methods for producing and screening for specific antibodies using hybridoma technology are routine and well known in the art. In a non-limiting example, mice can be immunized with a biomarker polypeptide or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention. The antibodies detecting neural biomarkers, peptides and derivatives thereof, can be used in immunoassays and other methods to identify new neural biomarkers and for use in the diagnosis of neural injury, degree of severity of injury and/or neurological disorders.

Other methods can also be used for the large scale production of neural biomarker specific antibodies. For example, antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., Gene 187 9-18 (1997); Burton et al., *Advances in Immunology* 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference.

The antibodies of the present invention have various utilities. For example, such antibodies may be used in diagnostic assays to detect the presence or quantification of the polypeptides of the invention in a sample. Such a diagnostic assay can comprise at least two steps. The first, subjecting a sample with the antibody, wherein the sample is a tissue (e.g., human, animal, etc.), biological fluid (e.g., blood, urine, sputum, semen, amniotic fluid, saliva, etc.), biological extract (e.g., tissue or cellular homogenate, etc.), a protein microchip (e.g., See Arenkov P, et al., *Anal Biochem.*, 278(2):123-131 (2000)), or a chromatography column, etc. And a second step involving the quantification of antibody bound to the substrate. Alternatively, the method may additionally involve a first step of attaching the antibody, either covalently, electrostatically, or reversibly, to a solid support, and a second step of subjecting the bound antibody to the sample, as defined above and elsewhere herein.

Various diagnostic assay techniques are known in the art, such as competitive binding assays, direct or indirect sandwich assays and immunoprecipitation assays conducted in either heterogeneous or homogeneous phases (Zola, Monoclonal Antibodies: A Manual of Techniques, CRC Press, Inc., (1987), pp147-158). The antibodies used in the diagnostic assays can be labeled with a detectable moiety. The detectable moiety should be capable of producing, either directly or indirectly, a detectable signal. For example, the detectable moiety may be a radioisotope, such as $^{2}H$, $^{14}C$, $^{32}P$, or $^{125}I$, a florescent or chemiluminescent compound, such as fluorescein isothiocyanate, rhodamine, or luciferin, or an enzyme, such as alkaline phosphatase, β-galactosidase, green fluorescent protein, or horseradish peroxidase. Any method known in the art for conjugating the antibody to the detectable moiety may be employed, including those methods described by Hunter et al., *Nature*, 144:945 (1962); David et al., *Biochem.*, 13:1014 (1974); Pain et al., *J. Immunol. Methods*, 40:219 (1981); and Nygren, *J. Histochem. Cytochem.*, 30:407 (1982).

Stem Cells

In another preferred embodiment, the methods of the invention are used for the repopulation of destroyed cells in an organ in need of repair. For example, brain, CNS, PNS, and the like. Any cell can be used in the methods of the invention, including but not limited to, stem cells, thymocytes, precursor cells and the like. A precursor cell population includes cells of a mesodermal derived cellular lineage, more particularly of hematopoietic lineage, endothelial lineage, muscle cell lineage, epithelial cell lineage and neural cell lineage.

In a preferred embodiment, molecular mediators for directed manipulation of stem/progenitor cells important for cell therapy and stimulation of endogenous neurogenesis are identified. For example, pro-survival lipid lysophosphatidic acid (LPA) instigated clonal generation of mouse neurospheres via LPA receptor-dependent proliferation of AC133 positive neural progenitors. Given a structural and receptor homology between LPA and endocannabinoids anandamide (AEA) and 2-arachidonoyl glycerol (2-AG), the endocannabinoid system may play a role in development of neural progenitors. A strong expression of cannabinoid receptors CB1 was found in mouse clonal neurospheres generated by ECF/FGF2 or LPA. CB1 receptor was expressed in the core of neurosphere and partially co-localized with LPA receptor and AC133. In neurospheres differentiated on an adherent matrix with EGF/FGF2, CB1 expression was restricted to cells of neuronal lineage. In contrast, neurospheres developed in the presence of LPA accumulated CB1 receptor in clusters of AC133 positive primitive progenitors.

In a preferred embodiment, a stem cell neurogenesis composition comprises endocannabinoids, LPA, AEA, 2-AG, and receptors thereof. Preferably, the endocannabinoids are anandamide(AEA) and 2-arachidonoyl glycerol (2-AG).

As discussed above, any cell can be used, preferably, the cells are stem cells. A "precursor cell" can be any cell in a cell differentiation pathway that is capable of differentiating into a more mature cell. As such, the term "precursor cell population" refers to a group of cells capable of developing into a more mature cell. A precursor cell population can comprise cells that are totipotent, cells that are pluripotent and cells that are stem cell lineage restricted (i.e. cells capable of developing into less than all hematopoietic lineages, or into, for example, only cells of neuronal lineage). As used herein, the term "totipotent cell" refers to a cell capable of developing into all lineages of cells. Similarly, the term "totipotent population of cells" refers to a composition of cells capable of developing into all lineages of cells. Also as used herein, the term "pluripotent cell" refers to a cell capable of developing into a variety (albeit not all) lineages and are at least able to develop into all neural cell lineages. For example, a pluripotent cell can differ from a totipotent cell by having the ability to develop into all cell lineages except endothelial cells. A "pluripotent population of cells" refers to a composition of cells capable of developing into less than all lineages of cells but at least into all hematopoietic lineages. As such, a totipotent cell or composition of cells is less developed than a pluripotent cell or compositions of cells. As used herein, the terms "develop", "differentiate" and "mature" all refer to the progression of a cell from the stage of having the potential to differentiate into at least two different cellular lineages to becoming a specialized cell. Such terms can be used interchangeably for the purposes of the present application.

The invention is of application without limitation to ES cell type, and may suitably be applied to vertebrate cells, in particular mammalian cells, primate cells, rodent cells, and human cells. By "ES" cells it is intended to encompass embryonic stem cells, embryonic carcinoma cells, embryonic gonadal cells, embryo-derived pluripotential stem cells and germline-derived stem cells.

As used herein, the term "population" refers to cells having the same or different identifying characteristics. The term "lineage" refers to all of the stages of the development of a cell type, from the earliest precursor cell to a completely mature cell (i.e. a specialized cell).

A stem cell population of the present invention is capable of developing into cells of mesodermal cell lineage, of ectodermal cell lineage or of endodermal cell lineage. As used herein, mesodermal cells include cells of connective tissue, bone, cartilage, muscle, blood and blood vessel, lymphatic and lymphoid organ, notochord, pleura, pericardium, peritoneum, kidney and gonad. Ectodermal cells include epidermal tissue cells, such as those of nail, hair, glands of the skin, the nervous system, the external sense organs (e.g., eyes and ears) and mucous membranes) such as those of the mouth and anus). Endodermal cells include cells of the epithelium such as those of the pharynx, respiratory tract (except the nose), digestive tract, bladder and urethra cells. Preferred cells within a stem cell population of the present invention include cells of at least one of the following cellular lineages: hematopoietic cell lineage, endothelial cell lineage, epithelial cell lineage, muscle cell lineage and neural cell lineage. Other preferred cells within a stem cell population of the present invention include cells of erythroid lineage, endothelial lineage, leukocyte lineage, thrombocyte lineage, erythroid lineage (including primitive and definitive erythroid lineages), macrophage lineage, neutrophil lineage, mast cell lineage, megakaryocyte lineage, natural killer cell lineage, eosinophil lineage, T cell lineage, endothelial cell lineage and B cell lineage.

Various techniques may be employed to separate the cells by initially removing cells of dedicated lineage. Monoclonal antibodies are particularly useful for identifying markers associated with particular cell lineages and/or stages of differentiation. If desired, a large proportion of terminally differentiated cells may be removed by initially using a "relatively crude" separation. For example, magnetic bead separations may be used initially to remove large numbers of lineage committed cells. Desirably, at least about 80%, usually at least 70% of the total hematopoietic cells will be removed.

Procedures for separation may include but are not limited to, magnetic separation, using antibody-coated magnetic beads, affinity chromatography, cytotoxic agents joined to a monoclonal antibody or used in conjunction with a monoclonal antibody, including but not limited to, complement and cytotoxins, and "panning" with antibody to a solid matrix, e.g., plate, elutriation or any other convenient technique. Techniques providing accurate separation include but are not limited to, flow cytometry, which can have varying degrees of sophistication, e.g., a plurality of color channels, low angle and obtuse light scattering detecting channels, impedance channels, etc.

In another preferred embodiment, the stem cells may be transformed with DNA which codes for different growth factors, cytokines, endocannabinoids, LPA, AEA, 2-AG, which will aid in the differentiation of the stem cells if the neural organ of interest is damaged to the extent that the microenvironment is not supportive of cell differentiation.

In another preferred embodiment, stem cells can be induced to differentiate into a desired phenotype by administering, endocannabinoids, LPA, AEA, 2-AG, growth factors, hormones, cytokines and the like. An illustrative example is provided in the Examples which follow.

In some applications, the cells expressing cannabinoid receptors and stem cells can be used to screen for drugs that will aid in the therapy of a patient suffering from neural injury and disorders, for example, subarachnoid hemorrhage, epilepsy, stroke, and other forms of brain injury. Stem cells can be used to screen for factors that induce the neurogenesis of the cells as compared to the cell differentiation produced or induced by endocannabinoids, LPA, AEA, 2-AG. For example, candidate maturation factors or growth factors are tested by adding them to system, and then determining any phenotypic change that results, according to desirable criteria for further culture and use of the cells.

Particular screening applications of this invention relate to the testing of pharmaceutical compounds in drug research. The reader is referred generally to the standard textbook "In vitro Methods in Pharmaceutical Research", Academic Press, 1997, and U.S. Pat. No. 5,030,015). Assessment of the activity of candidate pharmaceutical compounds generally involves administering a candidate compound, determining any change in the morphology, marker phenotype, or metabolic activity of the cells and function of the cells that is attributable to the compound (compared with untreated cells or cells treated with an inert compound), and then correlating the effect of the compound with the observed change.

The screening may be done, for example, either because the compound is designed to have a pharmacological effect on certain cell types, or because a compound designed to have effects elsewhere may have unintended side effects. Two or more drugs can be tested in combination (by combining with the cells either simultaneously or sequentially), to detect possible drug—drug interaction effects. In some applications, compounds are screened initially for potential toxicity (Castell et al., pp. 375-410 in "In vitro Methods in Pharmaceutical Research," Academic Press, 1997). Cytotoxicity can be determined in the first instance by the effect on cell viability, survival, morphology, and expression or release of certain markers, receptors or enzymes. Effects of a drug on chromosomal DNA can be determined by measuring DNA synthesis or repair. [$^3$H]thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (PP 375-410 in "In vitro Methods in Pharmaceutical Research," Academic Press, 1997) for further elaboration.

Compounds

In a preferred embodiment, the methods are used to screen for candidate drugs or compounds. The candidate drugs or compounds used in the present method are classified by protection against neural injury, neural disorders, subarachnoid hemorrhage, epilepsy, stroke, and other forms of brain injury. For example, TBI induces at sites of brain damage: (i) rapid activation of CB1 receptor and degradation of extracellular N-terminal parts, and (ii) concomitant CB1 receptor oligomerization via C-terminal domain in a time-dependent manner. Degradation of N-terminal parts of the CB1 results in sustained increase of N-specific oligomers in SCF. Within one hour, TBI instigates dramatic accumulation of a very high molecular weight CB1 oligomers via C-terminal domain followed by gradual decline at 14 day post injury. Thus, C-terminal CB1 oligomers in CSF represent a pathogenically relevant markers of TBI and may be used for monitoring effectivity of TBI treatment, including novel drugs targeting CB1 receptor such as Dronabinol. We have also shown that pro-survival lipid lysophosphatidic acid (LPA) instigated clonal generation of mouse neurospheres via LPA receptor-dependent proliferation of AC133 positive neural progenitors. Given a structural and receptor homology between LPA and endocannabinoids anandamide(AEA) and 2-arachidonoyl glycerol (2-AG), we suggested that the endocannabinoid system can play a role in development of neural progenitors. A strong expression of cannabinoid receptors CB1 was found in mouse clonal neurospheres generated by EGF/FGF2 or LPA. CB1 receptor was expressed in the core of neurosphere and partially co-localized with LPA receptor and AC133. In neurospheres differentiated on an adherent matrix with EGF/FGF2, CB1 expression was restricted to cells of neuronal lineage. In contrast, neurospheres developed in the presence of LPA accumulated CB1 receptor in clusters of AC133 positive primitive progenitors.

Synthetic endocannabinoids sustained growth of neurospheres from dissociated mouse and rat postnatal forebrain, while AM251, a selective CB1 receptor antagonist, abolished the generation of clonal neurospheres. Because AEA, 2-AG, LPA, and their receptors are up-regulated upon traumatic brain injury, and appear to be pro-survival and mitogenic for neural progenitors, the endocannabinoid/LPA system may play a role linking neuroprotection and neurogenesis during brain injury.

Candidate therapeutic compounds can be screened using these methods and compared to the effects of LPA, AEA, 2-AG, etc when administered to the cells. The most preferred compounds identified using the present method will be non-toxic, showing no reduction in viability between treated and non-treated cultures. However, low toxicity levels may be tolerable for certain uses (e.g., in initial compound testing and design). The compounds or therapeutic compositions can function to regenerate nerve cells, promote neurite outgrowth, and protect nerves from otherwise damaging treatments or conditions. Thus, the compounds and compositions of this invention are useful in the diagnosis, cure, mitigation, treatment, or prevention of neurological conditions in animals, including humans, and in animals (including humans) exposed to neurodegenerative agents or having damaged nervous system cells. Such conditions and disorders, when present in an animal, including humans, can be neurodegenerative disorders, neuropathic disorders, neurovascular disorders, traumatic injury of the brain, spinal cord, or peripheral nervous system, demyelinating disease of the central or peripheral nervous system, metabolic or hereditary metabolic disorder of the central or peripheral nervous system, or toxin-induced- or nutritionally related disorder of the central or peripheral nervous system. When present in a human, a neurodegenerative disorder can be, for example, Parkinson's disease, Alzheimer's disease, amyotrophic lateral sclerosis (ALS), Huntington's disease, cerebellar ataxia, or multisystem atrophy including, for example, olivopontocerebellar degeneration, striatonigral degeneration, progressive supranuclear palsy, Shy-Drager syndrome, spinocerebellar degeneration and corticobasal degeneration. A demyelinating disease can be, for example, multiple sclerosis, Guillain-Barre syndrome, or chronic inflammatory demyelinating polyradiculoneuropathy. A neurovascular disorder can be global cerebral ischemia, spinal cord ischemia, ischemic stroke, cardiogenic cerebral embolism, hemorrhagic stroke, lacunar infarction, multiple infarct syndromes including multiple infarct dementia, or any disorder resulting in ischemia or ischemia/reperfusion injury of the central nervous system. Traumatic injury of the central or peripheral nervous system can be, for example, concussion, contusion, diffuse axonal injury, edema, and hematoma associated with craniocerebral or spinal trauma, or axonal or nerve sheath damage associated with laceration, compression, stretch, or avulsion of peripheral nerves or plexi, and further includes nerve damage caused during surgery, such as prostate surgery. A neuropathic disorder can be, for example, diabetic neuropathy, uremic neuropathy, neuropathy related to therapy with drugs such as phenytoin, suramin, taxol, thalidomide, vincristine or vinblastine; or neuropathy/encephalopathy associated with infectious disease, such as, for example, encephalopathy related to HIV, rubella virus, Epstein-Barr virus, herpes simplex virus, toxoplasmosis, prion infection, A metabolic disorder of the central nervous system can be, for example, status epilepticus, hypoglycemia coma, or Wilson's disease.

Pharmaceutical Formulations and Routes of Administration

The compounds of the invention have utility in pharmacological compositions for the treatment and prevention of various neurological, subarachnoid hemorrhage, epilepsy, stroke, and other forms of brain injury, ischemic, and inflammatory disorders. The compounds also have utility in the treatment of traumatic injury to nervous tissue, or conditions associated with retinal and optic nerve damage. The compounds of the invention may be prepared as a salt or derivative, as described above.

A compound of the invention can be administered to an animal or human patient by itself or in pharmaceutical compositions where it is mixed with suitable carriers or excipients, at doses to treat or ameliorate various conditions. The compounds according to the present invention preferably have sufficient stability, potency, selectivity, solubility and availability to be safe and effective in treating diseases, injuries and other abnormal conditions or insults to the central nervous system including the brain, the peripheral nerves, and other organs. A therapeutically effective dose refers to that amount of the compound sufficient to affect an activity in a nerve or neuronal cell, to produce a detectable change in a cell or organism, or to treat a disorder in a human or other mammal. The word "treat" in its various grammatical forms as used in relation to the present invention refers to preventing, curing, reversing, attenuating, alleviating, minimizing, suppressing, ameliorating or halting the deleterious effects of a disease state, disease progression, injury, wound, ischemia, disease causative agent (e.g., bacteria, protozoans, parasites, fungi, viruses, viroids and/or prions), surgical procedure or other abnormal or detrimental condition (all of which are collectively referred to as "disorders," as will be appreciated by the person of skill in the art). A "therapeutically effective amount" of a compound according to the invention is an amount that can achieve effective treatment, and such amounts can be determined in accordance with the present teachings by one skilled in the art.

Therapeutically effective doses may be administered alone or as adjunctive therapy in combination with other treatments. Techniques for the formulation and administration of the compounds of the instant application may be found in Remington's Pharmaceutical Sciences, Mack Publishing Co., Easton, Pa., 18.sup.th edition (1990).

Suitable routes of administration may, for example, include oral, rectal, transmucosal, buccal, or intestinal administration; parenteral delivery, including intramuscular, subcutaneous, intramedullary injections, as well as intrathecal, direct intraventricular, intravenous, intraperitoneal, intranasal, or intraocular injections, and optionally in a depot or sustained release formulation. Furthermore, one may administer the agent of the present invention in a targeted drug delivery system, for example in a liposome coated with an antibody. The liposomes will be targeted to and taken up selectively by cells expressing the appropriate antigen.

The pharmaceutical compositions of the present invention may be manufacturing in a manner that is itself known, e.g., by means of conventional mixing, dissolving, emulsifying, encapsulating, entrapping, or lyophilizing processes. Pharmaceutical compositions for use in accordance with the present invention thus may be formulated in conventional manner using one or more physiologically acceptable carriers comprising excipients and auxiliaries, which facilitate processing of the active compounds into preparations, which can thus be used pharmaceutically.

For injection, the agents of the invention may be formulated in aqueous solutions, preferably in physiologically compatible buffers, such as Hank's solution, Ringer's solution, or physiological saline buffer. For transmucosal or buccal administration, penetrants appropriate to the barrier to be permeated may be used in the formulation. Such penetrants are known in the art.

For oral administration, the compounds can be formulated readily by combining the active compounds with pharmaceutically acceptable carriers, well known to those in the art. Such carriers enable the compounds of the invention to be formulated as tablets, pills, capsules, liquids, quick-dissolving preparations, gels, syrups, slurries, suspensions and the like, for oral ingestion by a patient to be treated. Pharmaceutical preparations for oral use of the compounds of this invention can be obtained by employing a solid excipient, optionally grinding a resulting mixture, and processing the mixture of granules, after adding suitable auxiliaries, if desired, to obtain tablets. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP).

In general, the pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. If desired, disintegrating agents may be added, such as the cross-linked polyvinyl pyrrolidone agar, or alginic acid or a salt thereof such as sodium alginate or a number of others disintegrants [see, for example, Remington's Pharmaceutical Sciences, Mack Publishing Co., Easton, Pa., 18.sup.th edition (1990)].

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, pressurized air, or other suitable gas or mixture. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly concentrated solutions. Alternatively, the active ingredient may be in powder form for reconstitution with a suitable vehicle, e.g., sterile pyrogen-free water, before use.

The compounds may also be formulated in rectal compositions such as suppositories, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compounds of the invention may further be formulated in pharmaceutical or cosmetic compositions for topical application to the skin in the form of an aqueous, alcoholic, aqueous/alcoholic or oily solution, or of a dispersion of the lotion or serum type, of an emulsion having a liquid or semi-liquid consistency of the milk type, obtained by dispersion of a fatty phase in an aqueous phase (O/W) or vice versa (W/O), or of a suspension or of an emulsion with a soft consistency of the aqueous or anhydrous gel, foam or cream type, or, alternatively, of microcapsules or microparticles, or of a vesicular dispersion of ionic and/or nonionic type, or may further be administered in the form of an aerosol composition comprising a pressurized propellant agent.

Liposomes and emulsions are well known examples of delivery vehicles or carriers for hydrophobic drugs. Certain organic solvents such as dimethylsulfoxide also may be employed. Additionally, the compounds may be delivered using a sustained-release system, such as semi permeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for stabilization may be employed.

Pharmaceutical compositions suitable for use in the present invention include compositions wherein the active ingredients are contained in an effective amount to achieve their intended purpose, to affect a therapeutic benefit, or to effect a detectable change in the function of a cell, tissue, or organ. More specifically, a therapeutically effective amount means an amount effective to prevent the development of or to alleviate the existing symptoms of the subject being treated. Determining the effective amount is well within the capability of those skilled in the art, especially in light of the detailed disclosure provided herein.

Toxicity and therapeutic efficacy of the compounds or compositions can be determined by standard pharmaceutical, pharmacological, and toxicological procedures in cell cultures or experimental animals. For example, numerous methods for determining the $LD_{50}$ (the dose lethal to 50% of the population) and the $ED_{50}$ (the dose therapeutically effective in 50% of the population) exist. The dose ratio between toxic and therapeutic effects is the therapeutic index, which can be expressed as the ratio between $LD_{50}$ and $ED_{50}$. Compounds and compositions exhibiting high therapeutic indices are preferred. The data obtained from cell culture assays or animal studies can be used in formulating a range of dosages for use in humans. [See, for example, Fingl et al., in The Pharmacological Basis of Therapeutics, Ch. 1 p. 1 (1975)].

The compounds of the present invention may be administered by a single dose, multiple discrete doses or continuous infusion. Some of the compounds preferably are non-peptidic, easily diffusible and relatively stable, they can be well-suited to continuous infusion.

Dose levels on the order of about 0.1 mg to about 10,000 mg of the active ingredient are useful in the treatment of the above conditions, with preferred levels being about 0.1 mg to about 1,000 mg. The specific dose level, and thus the therapeutically-effective amount, for any particular patient will vary depending upon a variety of factors, including the activity of the specific compound employed and its bioavailability at the site of drug action; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models also are helpful. The considerations for determining the proper dose levels are available to the skilled person.

Certain compounds can be administered in lyophilized form. In this case, 1 to 1000 mg of a compound of the present invention may be lyophilized in individual vials, together with a carrier and a buffer, such as mannitol and sodium phosphate. The compound may be reconstituted in the vials with bacteriostatic water before administration.

In treating neurological disorders resulting from global or focal ischemia, for example, the compounds of the present invention are preferably administered orally, rectally, parenterally or topically at least 1 to 6 times daily, and may follow an initial bolus dose of higher concentration.

For the compounds, methods, and uses of the present invention, any administration regimen regulating the timing and sequence of drug delivery can be used and repeated as necessary to effect treatment. Such regimen may include pretreatment and/or co-administration with additional therapeutic agents.

Kits

In yet another aspect, the invention provides kits for aiding a diagnosis of brain injury, TBI, subarachnoid hemorrhage, epilepsy, stroke, and other forms of brain injury, degree of severity of injury, subcellular localization and/or neuronal disorders, wherein the kits can be used to detect the markers of the present invention. For example, the kits can be used to detect any one or more of the markers described herein, which markers are differentially present in samples of a patient and normal subjects. The kits of the invention have many applications. For example, the kits can be used to differentiate if a subject has axonal injury versus, for example, dendritic, or has a negative diagnosis, thus aiding neuronal injury diagnosis. In another example, the kits can be used to identify compounds that modulate expression of one or more of the markers in in vitro or in vivo animal models to determine the effects of treatment.

In one embodiment, a kit comprises (a) an antibody that specifically binds to a marker; and (b) a detection reagent. Such kits can be prepared from the materials described above, and the previous discussion regarding the materials (e.g., antibodies, detection reagents, immobilized supports, etc.) is fully applicable to this section and will not be repeated. Optionally, the kit may further comprise pre-fractionation spin columns. In some embodiments, the kit may further comprise instructions for suitable operation parameters in the form of a label or a separate insert.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Optionally, the kit may further comprise a standard or control information so that the test sample can be compared with the control information standard to determine if the test amount of a marker detected in a sample is a diagnostic amount consistent with a diagnosis of neural injury, degree of severity of the injury, subcellular localization, neuronal disorder and/or effect of treatment on the patient.

In another embodiment, a kit comprises: (a) a substrate comprising an adsorbent thereon, wherein the adsorbent is suitable for binding a marker, and (b) instructions to detect the marker or markers by contacting a sample with the adsorbent and detecting the marker or markers retained by the adsorbent. In some embodiments, the kit may comprise an eluant (as an alternative or in combination with instructions) or instructions for making an eluant, wherein the combination of the adsorbent and the eluant allows detection of the markers using gas phase ion spectrometry. Such kits can be prepared from the materials described above, and the previous discussion of these materials (e.g., probe substrates, adsorbents, washing solutions, etc.) is fully applicable to this section and will not be repeated.

In another embodiment, the kit may comprise a first substrate comprising an adsorbent thereon (e.g., a particle functionalized with an adsorbent) and a second substrate onto which the first substrate can be positioned to form a probe which is removably insertable into a gas phase ion spectrometer. In other embodiments, the kit may comprise a single substrate which is in the form of a removably insertable probe with adsorbents on the substrate. In yet another embodiment, the kit may further comprise a pre-fractionation spin column (e.g., Cibacron blue agarose column, anti-HSA agarose column, size exclusion column, Q-anion exchange spin column, single stranded DNA column, lectin column, etc.).

Optionally, the kit can further comprise instructions for suitable operational parameters in the form of a label or a separate insert. For example, the kit may have standard instructions informing a consumer how to wash the probe after a sample is contacted on the probe. In another example, the kit may have instructions for pre-fractionating a sample to reduce complexity of proteins in the sample. In another example, the kit may have instructions for automating the fractionation or other processes.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in pertinent part for all purposes to the same extent as if each individual publication or patent document were so individually denoted. By their citation of various references in this document, Applicants do not admit any particular reference is "prior art" to their invention.

EXAMPLES

Materials and Methods

Abbreviations:

AEBSF, 4-(2-aminoethyl)-benzenesulfonylflouride; EDTA, ethylenediaminetetraacetic acid; EGTA, ethylene (oxyethylenenitrilo) tetra acetic acid; DMEM, Dulbecco's modified Eagle's medium; BSA, bovine serum albumin; DPBS, Dulbecco's phosphate buffered saline; DTT, dithiothreitol; FDA, fluorescein diacetate; GFAP, glial fibrillary acid protein; HBSS, Hanks' balanced salt solution; MAP-2, microtubule associated protein-2; PI, propidium iodide; PMSF, phenylmethylsulfonyl fluoride; SDS, sodium dedocyl sulfate; TEMED, N,N,N',N'-tetramethyletheylenediamine; CalpInh-II, calpain inhibitor II (N-acetyl-Leu-Leu-methioninal); Z-D-DCB, pan-caspase inhibitor(carbobenzoxy-Asp-CH2—OC (O)-2-6-dichlorobenzene); PBS, phosphate buffered saline; TLCK, Nα-p-tosyl-L-Lysine chloro methyl; TPCK, N-tosyl-L-phenylalanine chloromethyl ketone.

Surgical Procedures

Controlled cortical impact traumatic brain injury. A cortical impact injury device was used to produce TBI in rodents. Cortical impact TBI results in cortical deformation within the vicinity of the impactor tip associated with contusion, and neuronal and axonal damage that is constrained in the hemisphere ipsilateral to the site of injury. Adult male (280-300 g) Sprague-Dawley rats (Harlan; Indianapolis, Ind.) were initially anesthetized with 4% isoflurane in a carrier gas or 1:1 O2/N2O (4 min.) followed by maintenance anesthesia of 2.5% isoflurane in the same carrier gas. Core body temperature was monitored continuously by a rectal thermistor probe and maintained at 37±1° C. by placing an adjustable temperature controlled heating pad beneath the rats. Animals were mounted in a stereotactic frame in a prone position and secured by ear and incisor bars.

A midline cranial incision was made, the soft tissues were reflected, and a unilateral (ipsilateral to site of impact) craniotomy (7 mm diameter) was performed adjacent to the central suture, midway between bregma and lambda. The dura meter was kept intact over the cortex. Brain trauma in rats was produced by impacting the right cortex (ipsilateral cortex) with a 5 mm diameter aluminum impactor tip (housed in a pneumatic cylinder) at a velocity of 3.5 m/s with a 2.0 mm compression and 150 ms dwell time (compression duration). Velocity was controlled by adjusting the pressure (compressed N2) supplied to the pneumatic cylinder. Velocity and dwell time were measured by a linear velocity displacement transducer (Lucas Shaevitz™ model 500 HR; Detroit, Mich.) that produces an analogue signal that was recorded by a storage-trace oscilloscope (BK Precision, model 2522B; Placentia, Calif.). Sham-injured animals underwent identical surgical procedures but did not receive an impact injury. Appropriate pre- and post-injury management was maintained.

Preparation of Cortical Tissue and CSF

CSF and brain cortices were collected from animals at various intervals after sham-injury or TBI. At the appropriate time-points, TBI or sham-injured animals were anesthetized as described above and secured in a stereotactic frame with the head allowed to move freely along the longitudinal axis. The head was flexed so that the external occipital protuberance in the neck was prominent and a dorsal midline incision was made over the cervical vertebrae and occiput. The atlanto-occipital membrane was exposed by blunt dissection and a 25G needle attached to polyethylene tubing was carefully lowered into the cisterna magna. Approximately 0.1 to 0.15 ml of CSF was collected from each rat. Following CSF collection, animals were removed from the stereotactic frame and immediately killed by decapitation.

Ipsilateral and contralateral (to the impact site) cortices were then rapidly dissected, rinsed in ice cold PBS, and snap frozen in liquid nitrogen. Cortices beneath the craniotomies were excised to the level of the white matter and extended ~4 mm laterally and ~7 mm rostrocaudally. CSF samples were centrifuged at 4000 g for 4 min. at 4° C. to clear any contaminating erythrocytes. Cleared CSF and frozen tissue samples were stored at −80° C. until ready for use. Cortices were homogenized in a glass tube with a TEFLON dounce pestle in 15 volumes of an ice-cold triple detergent lysis buffer (20 mM Hepes, 1 mM EDTA, 2 mM EGTA, 150 mM NaCl, 0.1% SDS, 1.0% IGEPAL 40, 0.5% deoxycholic acid, pH 7.5) containing a broad range protease inhibitor cocktail (Roche Molecular Biochemicals, cat. #1-836-145).

Human CSF samples were obtained with informed consent from human subjects suffering from TBI, and from control patients without TBI, having hydrocephaly.

Gel Electrophoresis and Immunoblot Analyses of CSF

Protein concentrations of CSF were determined by bicinchoninic acid microprotein assays (Pierce Inc., Rockford, Ill.) with albumin standards. Protein balanced samples were prepared for sodium dodecyl sulfate-polyacrylamide gel electrophoresis (SDS-PAGE) in twofold loading buffer containing 0.25 M Tris (pH 6.8), 0.2 M DTT, 8% SDS, 0.02% bromophenol blue, and 20% glycerol in distilled $H_2O$. Samples were heated for 2 min. at 90° C. and centrifuged for 1 min. at 10,000 rpm in a microcentrifuge at ambient temperature. Twenty to forty micrograms of protein per lane was routinely resolved by SDS-PAGE on 6.5% Tris/glycine gels for 1 hour at 200V. Following electrophoresis, separated proteins were laterally transferred to polyvinylidene fluoride (PVDF) membranes in a transfer buffer containing 400 mM glycine and 0.025 M Tris (pH 8.9) with 5% methanol at a constant voltage of 125 V for 2 hour at 4° C. Blots were blocked for 1 hour at ambient temperature in 5% nonfat milk in TBST (25 mM TrisHCl pH 7.4, 150 mM NaCl, 0.05% Tween-20, 0.02% sodium azide).

Immunoblots containing brain or CSF protein were probed with an anti-neural protein specific primary antibodies (e.g. anti- CB1, CB2 antibodies etc., anti-UCH-L1, anti-alpha-synuclein and anti-p24). Following an overnight incubation at 4° C. with the primary antibodies in 5% nonfat milk in TBST, blots were incubated for 1 hour at ambient temperature in 5% nonfat milk that contained an alkaline phosphatase or horseradish peroxidase-conjugated goat anti-mouse IgG (1:10,000 dilution) or goat-anti-rabbit IgG (1:3000). Alkaline phosphatase-based colorimetric development (BCIP-NBT substrate) or enhanced chemiluminescence (ECL, Amersham) reagents were used to visualize immunolabeling on Kodak Biomax ML chemiluminescent film.

Assessing Neural Protein Release

SDS-Polyacrylamide (SDS-PAGE) gel electrophoresis and immunoblotting. At the end of an experiment, cells were harvested from 5 identical culture wells and collected in 15 ml centrifuge tubes and centrifuged at 3000 g for 5 min. The medium was removed and the pellet cells were rinsed with 1× DPBS. Cells were lysed in ice cold homogenization buffer [20 mM PIPES (pH 7.6), 1 mM EDTA, 2 mM EGTA, 1 mM DTT, 0.5 mM PMSF, 50 μg/mL Leupeptin, and 10 μg/mL each of AEBSF, aprotinin, pepstatin, TLCK and TPCK for 30 min., and sheared through a 1.0 mL syringe with a 25 gauge needle 15 times. Protein content in the samples was assayed by the Micro BCA method (Pierce, Rockford, Ill., USA).

For protein electrophoresis, equal amounts of total protein (30 μg) were prepared in two fold loading buffer containing 0.25 M Tris (pH 6.8), 0.2 M DTT, 8% SDS, 0.02% bromophenol blue, and 20% glycerol, and heated at 95° C. for 10 min. Samples were resolved in a vertical electrophoresis chamber using a 4% stacking gel over a 7% acrylamide resolving gel for 1 hour at 200V. For immunoblotting, separated proteins were laterally transferred to nitrocellulose membranes (0.45 μM) using a transfer buffer consisting of 0.192 M glycine and 0.025 M Tris (pH 8.3) with 10% methanol at a constant voltage (100 V) for 1 hour at 4° C. Blots were blocked overnight in 5% non-fat milk in 20 mM Tris, 0.15 M NaCl, and 0.005% Tween-20 at 4° C. Coomassie blue and Panceau red (Sigma, St. Louis, Mo.) were used to stain gels and nitrocellulose membranes (respectively) to confirm that equal amounts of protein were loaded in each lane.

Immunoblots were probed as described below with a primary antibody (e.g. anti-CB1 polyclonal antibody against C-terminal fragment of receptor raised in rabbit (Chemicon), anti-CB1 antibody against N-terminal (1-14a.a.) fragments of CB1 receptor (CaymanChem), or anti-CB1 polyclonal antibody against N-terminal fragment (1-77 a.a.) of CB1 receptor (Affinity). Following incubation with the primary antibody (1:2000) for 2 hours at room temperature, the blots were incubated in peroxidase-conjugated sheep anti-mouse IgG for 1 hour (1:10,000). Enhanced chemiluminescence reagents (ECL, Amersham) were used to visualize the immunolabeling on Hyperfilm (Hyperfilm ECL, Amersham).

Statistical Analyses

Quantitative evaluation of protein levels detected by immunoblotting was performed by computer-assisted densitometric scanning (ImageJ-NIH). Data were acquired as integrated densitometric values and transformed to percentages of the densitometric levels obtained on scans from sham-injured animals visualized on the same blot. Data was evaluated by least squares linear regression followed by ANOVA. All values are given as mean±SEM. Differences were considered significant if $p<0.05$.

Example 1

Endocannabinoids anandamide (AA) and 2-arachidonoyl-glycerol (2-AG) can be produced upon brain damage and, possibly instigate neuroprotective effect. AA and 2-AG act via G protein-coupled (GPCR) central type of cannabinoid receptors CB1, which undergo desensitization and internalization upon activation with AA or 2-AG. It is not clear whether CB1 receptor, like several other GPCR (e.g. GABAA-R, opiate-R), can form oligomeric complexes in the brain. CB1 receptors have not been characterized following traumatic brain injury (TBI). Therefore, the objective was to proteomic profiling of CB1 receptor complexes in rat cortex, hippocampus and CSF after TBI to ascertain its pathogenic and diagnostic significance.

Without wishing to be bound by theory, it is hypothesized that CB1 receptors occur in rat brain as both monomers and oligomeric complexes; TBI results in degradation of CB1 monomers and formation of oligomeric complexes in injured cortex and hippocampus; CB1 complexes may be accumulated in SCF and thereby provide a sensitive and pathogenically relevant markers of TBI.

An established model of rat TBI with cortical impact of 1.6 mm was employed. Brain cortex and hippocampus tissues were analyzed separately at various times after damage using Western blot, and immunohistochemistry. To distinguish N-terminal and C-terminal parts of CB1 receptor, several antibody generated against different domains of the CB1 receptor were used. FIG. 1 shows the CB1 antibody recognition sites at different N- and C-terminal motifs of rat CB1 and CB1A receptor. FIG. 2 shows the results obtained with CB1 Abs against N1-14 and N1-77 terminals motifs recognized mainly 62-64 kDa band in both cortex and hippocampus. The N84-97 domain-specific CB1 Abs labeled also a 120-130 kDa protein in the cortex in addition to 62-64 kDa CB1 protein. These proteins degraded upon traumatic insult in a time-dependent fashion and accumulated in CSF as ~260 kDa and 120-130 kDa proteins. FIG. 3 shows the results obtained with CB1 antibody against C-terminal domain recognized several molecular forms of CB1 immunoreactivity: ~42 kDa, 62-64 kDa, 120-130 kDa and >250 kDa both cortex and hippocampus. The 120-130 kDa protein decreased within 3 hours after TBI with concomitant accumulation of 260 kDa and >>260 kDa CB1 proteins. Intracellular C-domain-specific CB1 receptors accumulated in CSF as 120-130 kDa, ~260 kDa and >>260 kDa proteins. FIG. 4 shows the results obtained using immunohistochemistry with N-terminal and C-terminal Abs which revealed a decrease in N-positive staining and increase of C-terminal accumulation in cortex and hippocampus after TBI. Shown: CB1 (green)/NeuN (red) merged images (yellow). Arrows: co-localization of CB1 and NeuN; arrowheads: lack of or partial co-localization.

The results indicate that CB1 receptors occur in rat brain as both monomeric and oligomeric complexes, which differentially recognized by N-terminal and C-terminal-specific CB1 antibody. TBI induces at sites of brain damage: (i) rapid activation of CB1 receptor and degradation of extracellular N-terminal parts, and (ii) concomitant CB1 receptor oligomerization via C-terminal domain in a time-dependent manner. Degradation of N-terminal parts of the CB1 results in sustained increase of N-specific oligomers in SCF. Within one hour, TBI instigates dramatic accumulation of a very high molecular weight CB1 oligomers via C-terminal domain followed by gradual decline at 14 day post injury.

Thus, C-terminal CB1 oligomers in CSF represent a pathogenically relevant markers of TBI and may be used for monitoring effectivity of TBI treatment, including novel drugs targeting CB1 receptor such as Dronabinol.

Example 2

Cell Therapy and Neurogenesis

Identification of molecular mediators for directed manipulation of stem/progenitor cells is essential for cell therapy and stimulation of endogenous neurogenesis. We have shown that pro-survival lipid lysophosphatidic acid (LPA) instigated clonal generation of mouse neurospheres via LPA receptor-dependent proliferation of AC133 positive neural progenitors. Given a structural and receptor homology between LPA and endocannabinoids anandamide(AEA) and 2-arachidonoyl glycerol (2-AG), we suggested that the endocannabinoid system can play a role in development of neural progenitors. A strong expression of cannabinoid receptors CB1 was found in mouse clonal neurospheres generated by EGF/FGF2 or LPA. CB1 receptor was expressed in the core of neurosphere and partially co-localized with LPA receptor and AC133. In neurospheres differentiated on an adherent matrix with EGF/FGF2, CB1 expression was restricted to cells of neuronal lineage. In contrast, neurospheres developed in the presence of LPA accumulated CB1 receptor in clusters of AC133 positive primitive progenitors.

Figure 5A:
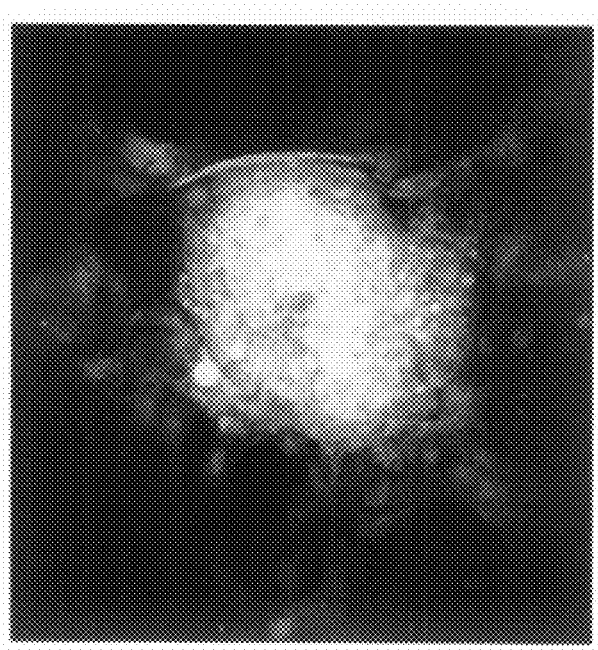
FIGS. 5A and 5B are images showing that CB1 receptor is expressed in LPA-generated neurospheres and co-localized with AC133 marker of neural stem cells.
Figure 5B:
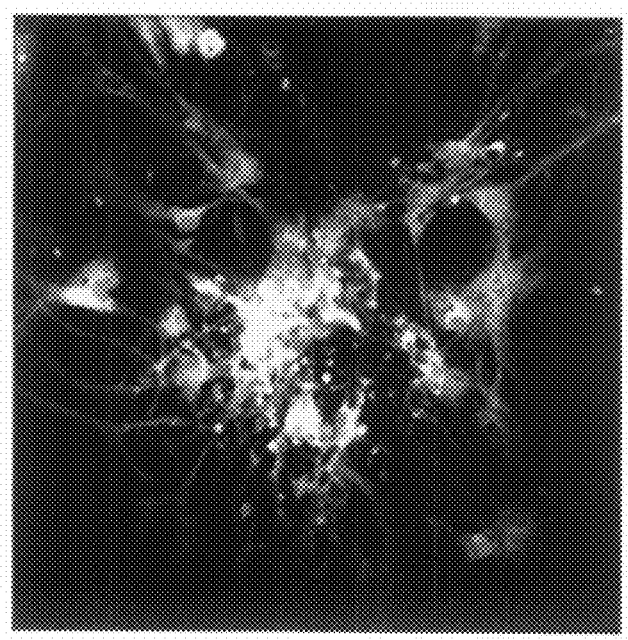

Interestingly, there was a partial co-localization of CB1 and GFAP in the core of the LPA neurospheres, suggesting a possible role of CB1 in astrocyte precursors. Finally, synthetic endocannabinoids sustained growth of neurospheres from dissociated mouse and rat postnatal forebrain, while AM251, a selective CB1 receptor antagonist, abolished the generation of clonal neurospheres. Because AEA, 2-AG, LPA, and their receptors are up-regulated upon traumatic brain injury, and appear to be pro-survival and mitogenic for neural progenitors, the endocannabinoid/LPA system may play a role linking neuroprotection and neurogenesis during brain injury. Results of the experiments are shown in FIGS. 5A-5B and 6A-6B. FIGS. 5A and 5B are images showing CB1 receptor is expressed in LPA-generated neurospheres and co-localized with AC133 marker of neural stem cells. FIG. 5A shows a neurosphere grown in suspension for 3 weeks. FIG. 5B shows an adherent developing neurosphere for 1 week. CB1-green, AC133-red; co-localization yellow.

Figure 6A:
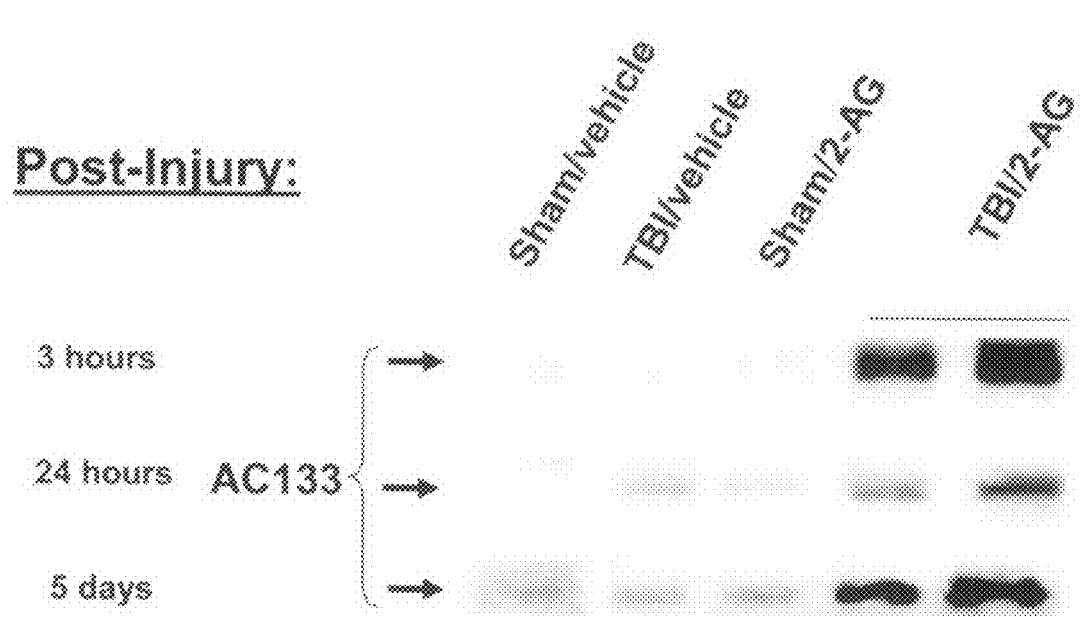
FIGS. 6A and 6B are blots showing up-regulation of AC133 (FIG. 6A) and Nestin (FIG. 6B) in brain cortex after TBI in mice treated with endocannabinoids 2-AG (i.p. 5 mg/kg daily) 3 hr, 24 hr and 5 days post injury.
Figure 6B:
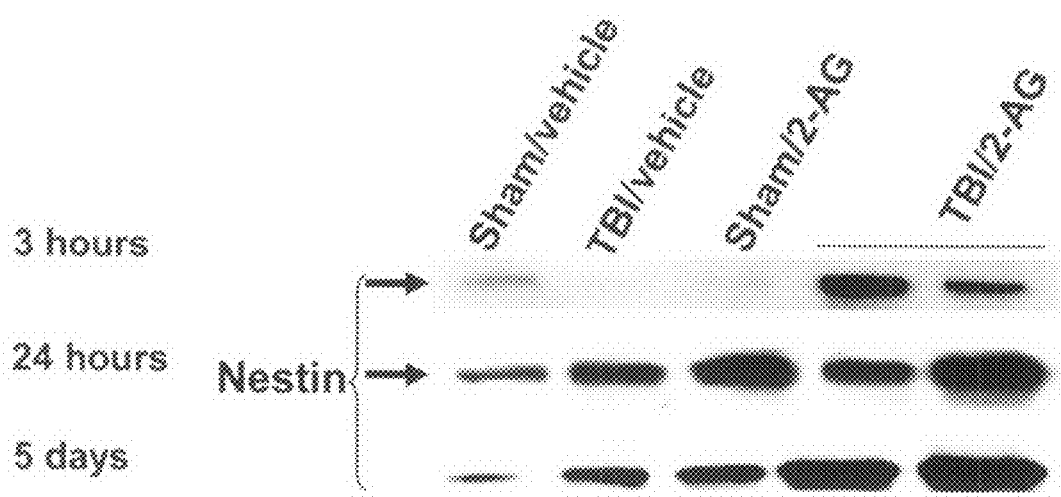
Figure 7A:
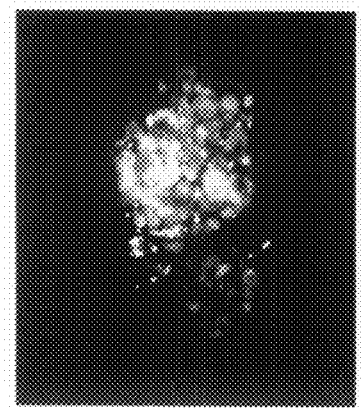
FIG. 7A shows expression of AC133/Sca-1 in LPA-generated clonal mouse neurospheres.
Figure 7B:
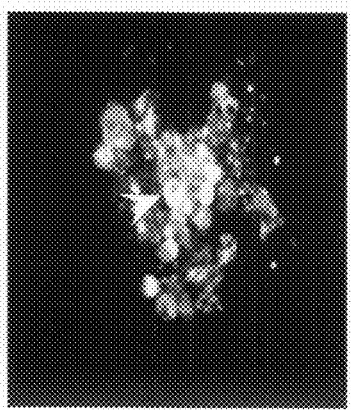
FIG. 7B shows expression of LPA1/LPA3 receptors in LPA-generated clonal mouse neurospheres.
Figure 7C:
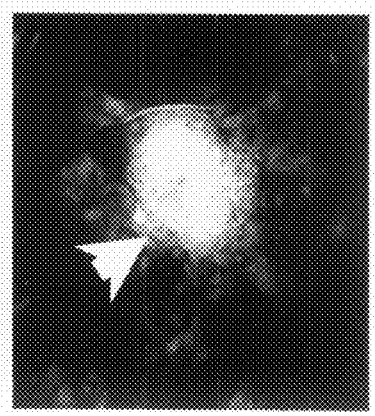
FIG. 7C shows expression of CB1/AC133 receptors in LPA-generated clonal mouse neurospheres.
Figure 8A:
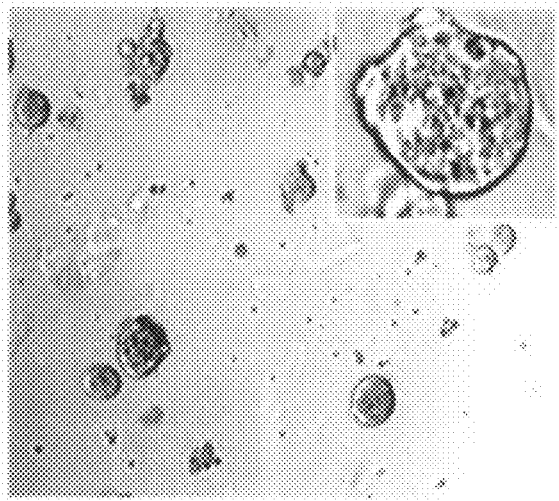
FIG. 8A shows abolition of clonal neurospheres from postnatal rat forebrain by CB1 antagonist endocannabinoid 2-AG at 1 µM.
Figure 8B:
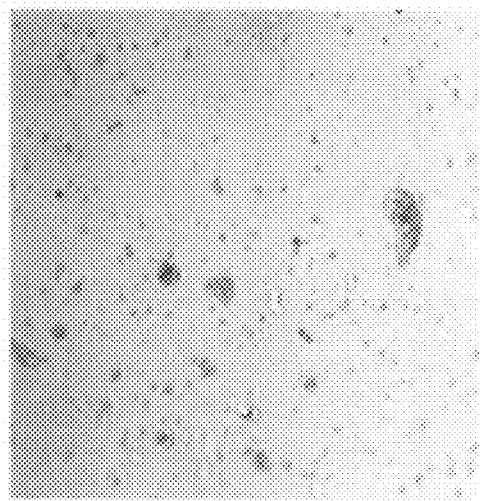
FIG. 8B shows effect of selective CB1 receptor antagonist AM251 (5 µM) on the formation of clonal neurospheres from postnatal rat forebrain.
Figures 9A, 9B:
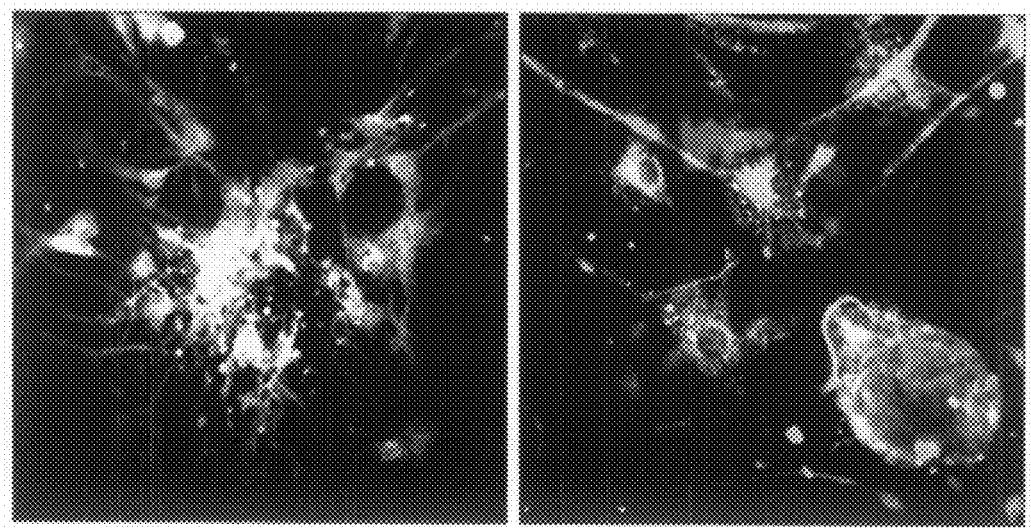
FIG. 9A shows expression and presentation of CB1 receptors in AC133 positive cells.
FIG. 9B shows expression and presentation of CB1 receptors in CFAP-positive astrocyte lineage of neurosphere core.
Figure 10A:
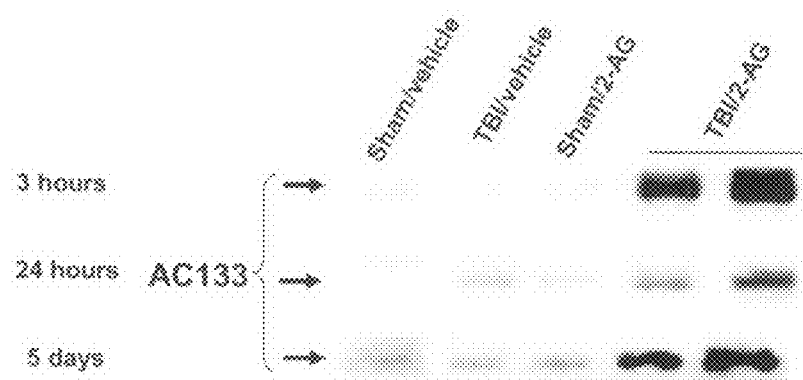
FIG. 10A shows increase of enhanced expression of AC133 neural stem cells after traumatic brain injury in mice as result of treatment post injury with endocannaboid 2-AG (5 mg/kg i.p. daily).
Figure 10B:
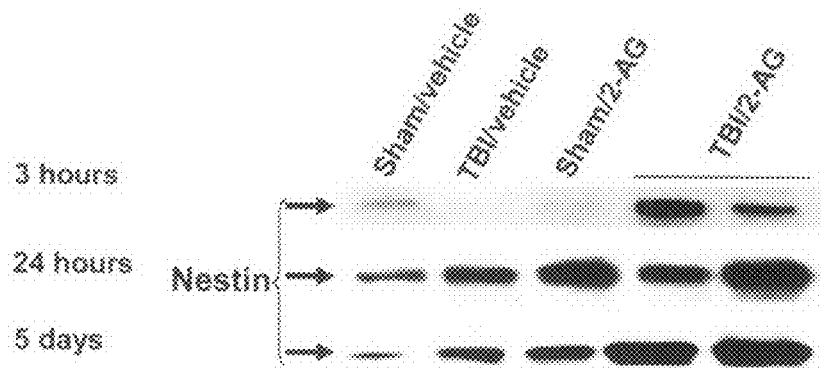
FIG. 10B shows increase of enhanced expression of nestin in neural stem cells after traumatic brain injury in mice as result of treatment post injury with endocannaboid 2-AG (5 mg/kg i.p. daily).

FIGS. 6A and 6B are blots showing up-regulation of AC133 (FIG. 6A) and Nestin (FIG. 6B) in brain after TBI in mice treated with endocannabinoids 2-AG (i.p. 5 mg/kg daily).

Example 3

Endoantibodiess, and Their Receptors in the Development of Neural Progenitors

Identification and characterization of endogenous molecules which stimulate proliferation/differentiation of neural stem cells is crucial for development of novel treatments for devastating diseases. We have recently discovered that lysophosphatidic acid (LPA), a precursor of endocannabinoid 2-AG, and 2-AG itself instigated clonal generation of neurospheres from dissociated mouse postnatal forebrain. Clonal expansion of these cells by LPA and 2-AG was inhibited by DGPP and AM251, antagonists of LPA and CB1 receptors, respectively. Potential roles for endocannabinoids anandamide and 2-AG in neural progenitor development, particularly after brain injury, has not been studied. We hypothesize that expression of CB1 receptors and up-regulation of endocannabinoids, represents a crucial mechanism of neural progenitor activation during brain injury, and that endocannabinoids are endogenous mediators which may enhance survival, increase motility and regulate proliferation and differentiation of neural progenitors, thus promoting brain development after injury. We are: (1) characterizing the endocannabinoid system in the development of neural progenitors from normal and CB1 deficient mice in culture; and (2) establishing the roles for endocannabinoids in the development of neural progenitors after traumatic brain injury (TBI) in mice. This will establish endocannabinoid-dependent mechanisms responsible for regulation of neural progenitors after brain injury, thus providing experimental rationale for improved treatment strategies for brain damage.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for determining the presence of traumatic brain injury (TBI), comprising analyzing for cannabinoid receptor type 1 (CB1) extracellular N-terminal and C-terminal biomarker proteins selected from the group consisting of 40-42 kDa, 62-64 kDa, 120-130 kDa, and >260 kDa monomeric or multimeric CB1 complexes in a cerebral spinal fluid (CSF), hippocampal, cortical or serum sample from a subject suspected of having TBI within and up to about 14 days from the TBI; and comparing levels of the biomarker proteins in a comparable sample from a normal subject;

wherein levels of extracellular N-terminal biomarker CB1 proteins are decreased and levels of the C-terminal biomarker CB1 proteins are increased in the sample of the subject suspected of having TBI compared to comparable samples from normal subjects.

2. The method of claim 1, wherein the 120-130 kDa protein biomarker levels are decreased within 3 hours of TBI in the TBI subject.

3. The method of claim 1, wherein accumulation of high molecular weight CB1 C-terminal domain molecular weight levels of oligomers with kDa greater than 260 in the sample from the subject suspected of having TBI compared to oligomer levels in a normal subject is indicative of TBI.

4. The method of claim 3, wherein the oligomers with molecular weights greater than 260 kDa accumulate within 3 hours of TBI.

5. The method of claim 1, wherein high molecular weight CB1 C-terminal domain oligomers greater than 260 kDa accumulate within one hour of TBI with a gradual decline up to 14 days post injury in the subject having TBI compared to levels of the oligomers in normal subjects.

6. The method of claim 1, wherein TBI is indicated by a decrease in N-terminal staining and an increase in C-terminal staining of the CB1 complexes in cortex or hippocampus tissue samples compared to staining in a comparable sample from a normal subject.

7. The method of claim 1, wherein the analyzing is with N-terminal and C-terminal specific CB1 antibodies.

8. The method of claim 1, wherein the sample is cerebrospinal fluid (CSF), cortex tissue or hippocampus tissue.

9. The method of claim 8, wherein the tissue sample is brain cortex or hippocampus.

10. The method of claim 8, wherein the sample is CSF.

11. The method of claim 1, wherein the sample is blood.

* * * * *

UNITED STATES PATENT AND TRADEMARK OFFICE
CERTIFICATE OF CORRECTION

PATENT NO.        : 7,611,858 B1
APPLICATION NO. : 11/738159
DATED             : November 3, 2009
INVENTOR(S)       : Stanislav Svetlov, Ronald L. Hayes and Ka-Wang Kevin Wang It is certified that error appears in the above-identified patent and that said Letters Patent is hereby corrected as shown below:

Column 2,
Line 14, "and O-type" should read --and Q-type--.

Column 7,
Line 18, "CFAP-positive" should read --GFAP-positive--.
Line 51, "neural injury a as compared to" should read --neural injury as compared to--.

Column 8,
Line 38, "understood to encompasses" should read --understood to encompass--.

Column 9,
Line 45, "in absolute amount" should read --an absolute amount--.

Column 11,
Line 8, " "Fc" of an antibody" should read --"Fc" portion of an antibody--.
Line 11, "$C_3$" should read --$CH_3$--.

Column 13,
Line 13, "which is approaches a" should read --which approaches a--.

Column 14,
Line 62, "patients to signs of" should read --patients for signs of--.

Column 15,
Lines 26-27, "systems, including nerve cells" should read
    --systems (including nerve cells--.

Column 16,
Line 21, "multiple sclerosis (MS," should read --multiple sclerosis (MS),--.
Line 30, "provides receptor molecules" should read --provides reporter molecules--.

Column 18,
Lines 11-12, "between the donor an acceptor" should read
    --between the donor and acceptor--.

Column 20,
Lines 36-37, "New Methods an Applications" should read
    --New Methods and Applications--.

CERTIFICATE OF CORRECTION (continued)
U.S. Pat. No. 7,611,858 B1

Column 21,
Line 31, "is an natural" should read --is a natural--.

Column 22,
Line 11, "encoding a such a polypeptide" should read --encoding such a polypeptide--.

Column 30,
Line 25, "method SELDI" should read --method known in the art. This includes, for example, mass spectrometry, fluorescence, surface plasmon resonance, ellipsometry and atomic force microscopy. Mass spectrometry, and particularly SELDI--.

Column 34,
Line 49, "aubarachnoid" should read --subarachnoid--.

Column 42,
Line 27, "by ECF/" should read --by EGF/--.

Column 43,
Line 22, "membranes) such" should read --membranes (such--.

Column 44,
Line 22, "5,030,015)." should read --5,030,015.--.

Column 47,
Line 7, "may be manufacturing" should read --may be manufactured--.

Column 51,
Line 48, "EGTA, ethylene" should read --EGTA, ethylenebis--.
Line 56, "N,N,N',N'-tetramethyletheylenediamine" should read --N,N,N',N'-tetramethylethylenediamine--.

Column 56,
Line 3, "Endoantibodiess," should read --LPA, Endocannabinoids,--.

Signed and Sealed this

Thirtieth Day of March, 2010

David J. Kappos
*Director of the United States Patent and Trademark Office*